(12) United States Patent
Lovley et al.

(10) Patent No.: US 11,066,449 B2
(45) Date of Patent: Jul. 20, 2021

(54) MICROBIAL NANOWIRES WITH INCREASED CONDUCTIVITY AND REDUCED DIAMETERS

(71) Applicant: University of Massachusetts, Boston, MA (US)

(72) Inventors: Derek R. Lovley, Amherst, MA (US); Nikhil Malvankar, New Haven, CT (US); Ramesh Adhikari, Amherst, MA (US); Yang Tan, Durham, NC (US); Joy Ward, Sunderland, MA (US); Kelly Nevin, Amherst, MA (US)

(73) Assignee: University of Massachusetts, Boston, MA (US)

( * ) Notice: Subject to any disclaimer, the term of this patent is extended or adjusted under 35 U.S.C. 154(b) by 565 days.

(21) Appl. No.: 15/744,116

(22) PCT Filed: Jul. 19, 2016

(86) PCT No.: PCT/US2016/043018
§ 371 (c)(1),
(2) Date: Jan. 12, 2018

(87) PCT Pub. No.: WO2017/015306
PCT Pub. Date: Jan. 26, 2017

(65) Prior Publication Data
US 2018/0371029 A1    Dec. 27, 2018

Related U.S. Application Data

(60) Provisional application No. 62/194,329, filed on Jul. 20, 2015.

(51) Int. Cl.
*C07K 14/195*    (2006.01)
*H01B 1/12*    (2006.01)

(52) U.S. Cl.
CPC ............. *C07K 14/195* (2013.01); *H01B 1/12* (2013.01)

(58) Field of Classification Search
None
See application file for complete search history.

(56) References Cited

U.S. PATENT DOCUMENTS

| | | | |
|---|---|---|---|
| 7,498,155 | B2 | 3/2009 | Lovley et al. |
| 8,729,233 | B2 | 5/2014 | Reguera et al. |
| 8,846,890 | B2 | 9/2014 | Reguera et al. |
| 2012/0053319 | A1* | 3/2012 | Reguera ................ B82Y 5/00 530/324 |
| 2014/0336357 | A1 | 11/2014 | Reguera et al. |

OTHER PUBLICATIONS

Richter et al. 2011 (Mutational analysis of geopilin function in Geobacter sulfurreducens; 2011 Dissertation; University of Massachusetts, Amherst) (Year: 2011).*
Richter 2011; Mutational Analysis of Geopilin Function in Geobacter sulfurreducens; Dissertation University of Massachusetts; Open Access Dissertations. 378. https://scholarworks.umass.edu/open_access_dissertations/378; (Year: 2011).*
Reardon et al. 2013 (Structure of the type IVa major pilin from the electrically conductive bacterial 2-4 nanowires of Geobacter sulfurreducens; Journal of Biological Chemistry 288: 41: 29260-29266). (Year: 2013).*
Malvankar et al., "Tunable metallic-like conductivity in microbial nanowires", Nature Nanotechnology, vol. 6, Sep. 2011, pp. 573-579.
Malvankar et al., "Microbial Nanowires: A New Paradigm for Biological Electron Transfer and Bioelectronics", ChemSusChem Concepts, vol. 5, 2012, pp. 1039-1046.
Malvankar et al., "Lack of cytochrome involvement in long-range electron transport through conductive biofilms and nanowires of Geobacter sulfurreducens", Energy & Environmental Science, vol. 5, 2012, pp. 8651-8659.
Vargas et al., "Aromatic Amino Acids Required for Pili Conductivity and Long-Range Extracellular Electron Transport in Geobacter sulfurreducens", mBio, vol. 4, Issue 2, Mar./Apr. 2013, pp. 1-6.
Liu et al., "A Geobacter sulfurreducens Strain Expressing Pseudomonas aeruginosa Type IV Pili Localizes OmcS on Pili but is Deficient in Fe(III) Oxide Reduction and Current Production", Applied and Environmental Microbiology, vol. 80, No. 3, Feb. 2014, pp. 1219-1224.
Malvankar et al., "Microbial nanowires for bioenergy applications", Current Opinion in Biotechnology, vol. 27, 2017, pp. 88-95.
Malvankar et al., "Visualization of charge propagation along individual pili proteins using ambient electrostatic force microscopy" Nature Nanotechnology, vol. 9, Dec. 2014, pp. 1-10.
Malvankar et al., "Structural Basis for Metallic-Like Conductivity in Microbial Nanowires", mBio, vol. 4, Issue 2, Mar./Apr. 2015, pages. mBio 6:e00084-00015.
Lovley et al., "Seeing is believing: novel imaging techniques help clarify microbial nanowire structure and function", Environmental microbiology, vol. 17, Issue 7, 2015, pp. 2209-2215.
Shih et al., "Tryptophan-Accelerated Electron Flow Through Proteins", Science, vol. 320, Jun. 27, 2008, pp. 1760-1762.
Coppi et al., "Development of a Genetic System for Geobacter sulfurreducens", Applied and Environmental Microbiology, vol. 67, No. 7, Jul. 2001, pp. 3180-3187.

(Continued)

*Primary Examiner* — Mary Maille Lyons
(74) *Attorney, Agent, or Firm* — Hamilton, Brook, Smith & Reynolds, P.C.

(57) ABSTRACT

Improved electrically conductive pili were generated from a natural pilus protein from the microorganism *Geobacter sulfurreducens*. Substituting a tryptophan for the phenylalanine at position F51 and a tryptophan for the tyrosine at position Y57 of the pilus monomer substantially increased the conductivity of the pili and reduced their diameter to 1.5 nm. Substantial improvements in conductivity were also achieved by substituting an additional tyrosine, histidine, and phenylalanine in the pilus monomer to mimic the monomer of *Geobacter metallireducens*, but the pili retained the typical *Geobacter sulfurreducens* wild-type diameter of 3 nm.

11 Claims, 18 Drawing Sheets

Specification includes a Sequence Listing.

(56) References Cited

OTHER PUBLICATIONS

Childers et al., "Geobacter metallireducens accesses insoluble Fe(III) oxide by chemotaxis" Nature, vol. 416, Apr. 18, 2002, pp. 767-769.
Reguera et al., "Extracellular electron transfer via microbial nanowires", Nature, vol. 435, Jun. 2005, pp. 1098-1101.
Nevin et al., "Anode Biofilm Transcriptomics Reveals Outer Surface Components Essential for High Density Current Production in Geobacter sulfurreducens Fuel Cells", PLoS One, vol. 4, Issue 5, May 2009, pp. 1-11.
Nevin et al., "Power output and columbic efficiencies from biofilms of Geobacter sulfurreducens comparable to mixed community microbial fuel cells", Environmental Microbiology, vol. 10, No. 10, 2008, pp. 2505-2514.
International Search Report for corresponding International Application No. PCT/2016/043018 dated Apr. 14, 2017.
Written Opinion of the International Searching Authority for corresponding International Application No. PCT/2016/043018 dated Apr. 14, 2017.
Richter, "Mutational Analysis of Geopilin Function in Geobacter Sulfurreducens", 2011,[retrieved online Dec. 28, 2016] at <http://scholarworks.umass.edu/open_access_dissertations/378/], 157 pages.
Reardon et al., "Structure of the Type IVa Major Pilin from the Electrically Conductive Bacterial Nanowires of Geobacter sulfurreducens", Journal of Biological Chemistry, vol. 288, No. 41, 2013, pp. 29260-29266.

\* cited by examiner

FTLIELLIVVAIIGILAAIAIPQFSAYRVKAYNSAASSDLRNLKTALESAFADDQTYPPES (SEQ ID NO 19)

FIG. 1

Tryptophans were Substituted for the Phenylalanine at Position 51 and the Tyrosine at Position 57 to Construct Strain W51W57

FTLIELLIVVAIIGILAAIAIPQFSAYRVKAYNSAASSDLRNLKTALESAWADDQTWPPES (SEQ ID NO 20)

F = Phenylalanine  Y = Tryosine  W = Tryptophane

FIG. 2

FIG. 6 Transmission Electron Micrograph of *Geobacter sulfurreducens* Cells Expressing the W51W57 Pili FIG. 15A
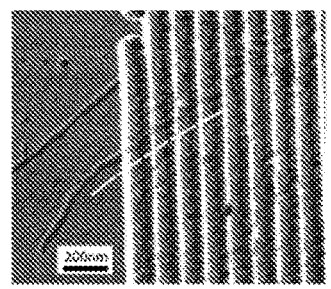
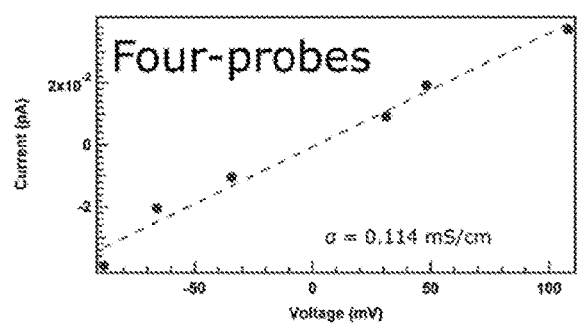
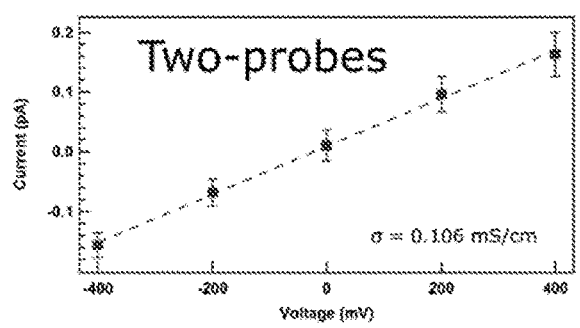
FIG. 15B
FIG. 15C

FIG. 16

*G. sulfurreducens*
FTLIELLIVAIIGILAAIAIPQFSAYRVKAVNSAASSDLRNLKTALESAFADIQTYPPES

*G. metallireducens*
FTLIELLIVAIIGILAAIAIPQFAAYRQKAFNSAAESDLKNTKTMLESVYSEIIQFYPA—

FIG. 18A
FIG. 18B
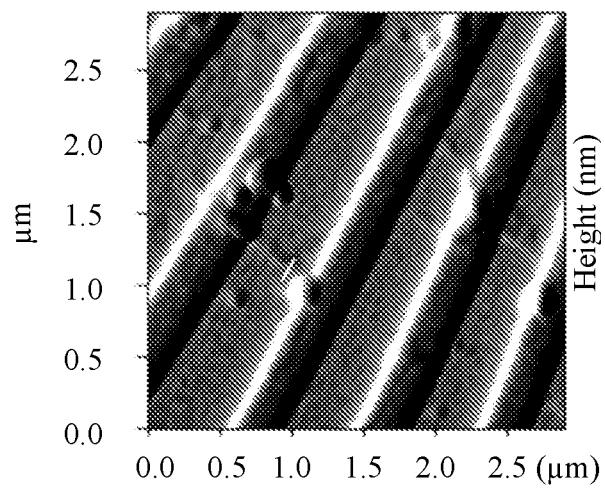
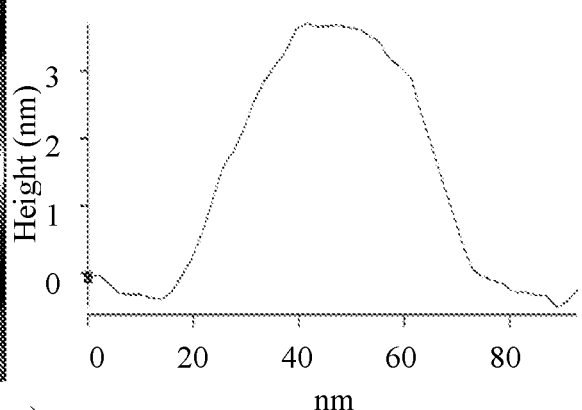
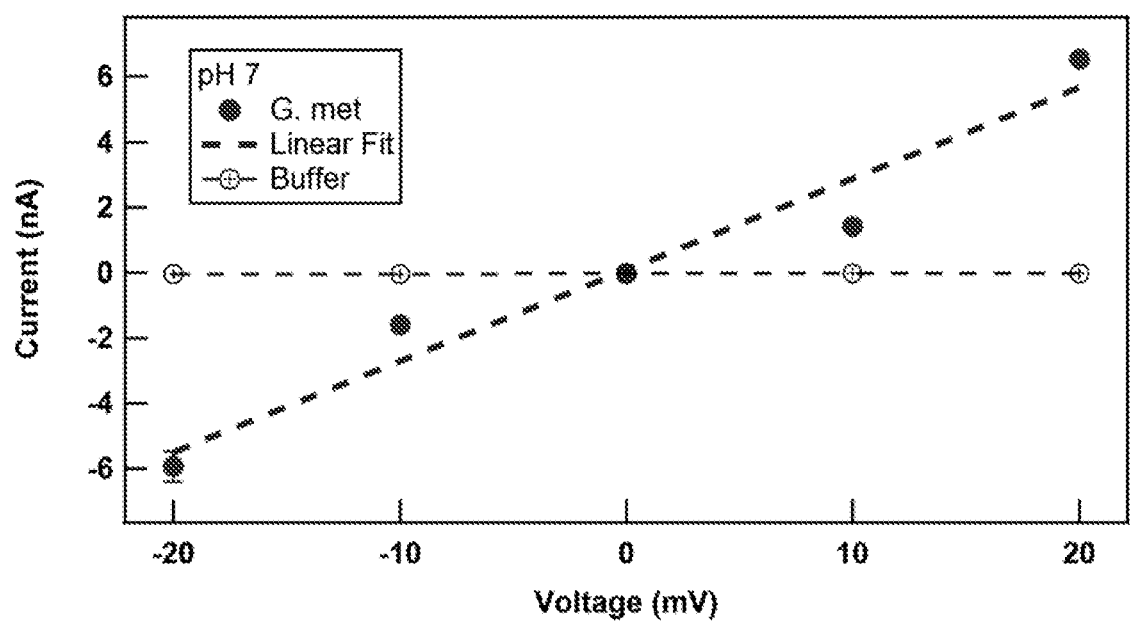
FIG. 18C

SEQUENCE LISTING

<160> NUMBER OF SEQ ID NOS: 23

<210> SEQ ID NO 1

```
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaaaactcg agagaggagc cagtgacgaa aatc                                   34

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctttcgggcg gccaggtttg atcatcagcc catgcggact caagag                      46

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcttgagtc cgcatgggct gatgatcaaa cctggccgcc cgaaag                      46

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaaaaagggc ccacgagact gacccaatcc aacaag                                 36

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggagccagt gacgaaaatc                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcttcccgta tgcccaactt                                                   20

<210> SEQ ID NO 7
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
attccgtatt gagcggggaa                                                   20

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttcctaagt ttctgtagca taagtgtctc ctttcttctt tt                          42

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaaagaagaa aggagacact tatgctacag aaacttagga ac                          42

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctccagtatg tatttaatca attaaagtgc attttccag tt                           42

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aactggaaaa atgcacttta attgattaaa tacatactgg ag                          42

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaacaggggc ccacgagact gacccaatcc aacaag                                 36

<210> SEQ ID NO 13
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13
aaaaaatcat gaaccgagct cggatccagg tg                                    32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaaaaagtcg catagggcg aattgggccc tc                                     32

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacttatgct acagaaactt ag                                               22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aatcaattaa agtgcatttt tc                                               22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tggacgaaat cggagaagtg c                                                21

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagatgtaag agccggcaaa tac                                              23

<210> SEQ ID NO 19
<211> LENGTH: 61
<212> TYPE: PRT
<213> ORGANISM: Geobacter sulfurreducens
```

<400> SEQUENCE: 19

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60

<210> SEQ ID NO 20
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Trp Ala Asp Asp Gln Thr Trp Pro Pro Glu Ser
    50                  55                  60

<210> SEQ ID NO 21
<211> LENGTH: 273
<212> TYPE: DNA
<213> ORGANISM: Geobacter sulfurreducens

<400> SEQUENCE: 21
ttggccaatt accccatac cccaacacaa gcagcaaaaa gaagaaagga gacacttatg      60
cttcagaaac tcagaaacag gaaaggtttc acccttatcg agctgctgat cgtcgttgcg    120
atcatcggta ttctcgctgc aattgcgatt ccgcagttct cggcgtatcg tgtcaaggcg    180
tacaacagcg cggcgtcaag cgacttgaga aacctgaaga ctgctcttga gtccgcattt    240
gctgatgatc aaacctatcc gcccgaaagt taa                                  273

<210> SEQ ID NO 22
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ttggccaatt accccatac cccaacacaa gcagcaaaaa gaagaaagga gacacttatg      60
cttcagaaac tcagaaacag gaaaggtttc acccttatcg agctgctgat cgtcgttgcg    120
atcatcggta ttctcgctgc aattgcgatt ccgcagttct cggcgtatcg tgtcaaggcg    180
tacaacagcg cggcgtcaag cgacttgaga aacctgaaga ctgctcttga gtccgcatgg    240
gctgatgatc aaacctggcc gcccgaaagt taa                                  273

<210> SEQ ID NO 23

```
<211> LENGTH: 59
<212> TYPE: PRT
<213> ORGANISM: Geobacter metallireducens

<400> SEQUENCE: 23

Phe Thr Leu Ile Glu Leu Leu Ile Val Val Ala Ile Ile Gly Ile Leu
1               5                   10                  15

Ala Ala Ile Ala Ile Pro Gln Phe Ala Ala Tyr Arg Gln Lys Ala Phe
            20                  25                  30

Asn Ser Ala Ala Glu Ser Asp Leu Lys Asn Thr Lys Thr Asn Leu Glu
        35                  40                  45

Ser Tyr Tyr Ser Glu His Gln Phe Tyr Pro Asn
    50                  55
```

MICROBIAL NANOWIRES WITH INCREASED CONDUCTIVITY AND REDUCED DIAMETERS

CROSS-REFERENCE TO RELATED APPLICATIONS

This application is a national phase of International Application No. PCT/US016/043018 filed Jul. 19, 2016, and published in the English language, and claims priority to and the benefit of U.S. Patent Application No. 62/194,329, filed Jul. 20, 2015, which applications are incorporated herein by reference in their entirety.

STATEMENT REGARDING FEDERALLY FUNDED RESEARCH OR DEVELOPMENT

This invention was made with government support under Contract No. N000141310549 awarded by the Office of Naval Research. The government has certain rights in the invention.

SEQUENCE LISTING

The instant application contains a Sequence Listing which has been submitted electronically in ASCII format and is hereby incorporated by reference in its entirety. Said ASCII copy, created on Jul. 29, 2020, is named 46821016002_Sub_Sequence_Listing.txt and is 8 KB in size.

FIELD OF THE INVENTION

The invention relates to electrically conductive materials in general and particularly to organic electrically conductive materials.

BACKGROUND OF THE INVENTION

Lovley et al., U.S. Pat. No. 7,498,155, issued Mar. 3, 2009, which is said to disclose conductive nanowires, as are available from a range of bacteria species, methods of use and related device structures, is a patent that describes some of the general features of conductive microbial nanowires.

Also known in the prior art is Reguera et al., U.S. Pat. No. 8,729,233, issued May 20, 2014, which is said to disclose a nanowire comprising a purified protein filament, such as a pilus, isolated from a bacterium, such as *Geobacter sulfurreducens*. Such a purified pilus can contain peptide subunits capable of assembling into the protein filament and establishing an electrical connection with an insoluble electron acceptor. The novel nanowires can be produced via a novel single step. Such nanowires are useful in applications requiring rectifying behavior.

Also known in the prior art is Reguera et al., U.S. Pat. No. 8,846,890, issued Sep. 30, 2014, which is said to disclose electrically conductive nanowires, as well as genetically and/or chemically modified nanowires with modified conductive, adhesive and/or coupling properties.

Also known in the prior art is Reguera et al., U.S. Patent Application Publication No. 20140336357 A1, published Nov. 13, 2014, which is said to disclose electrically conductive nanowires, as well as genetically and/or chemically modified nanowires with modified conductive, adhesive and/or coupling properties.

Some recent articles that are relevant include:

Malvankar, N. S., M. Vargas, K. P. Nevin, A. E. Franks, C. Leang, B.-C. Kim, K. Inoue, T. Mester, S. F. Covalla, J. P. Johnson, V. M. Rotello, M. T. Tuominen, and D. R. Lovley. 2011. Tunable metallic-like conductivity in nanostructured biofilms comprised of microbial nanowires. Nature Nanotechnology 6:573-579.

Vargas, M., N. S. Malvankar, P.-L. Tremblay, C. Leang, J. A. Smith, P. Patel, O. Synoeyenbos-West, K. P. Nevin, and D. R. Lovley. 2013. Aromatic amino acids required for pili conductivity and long-range extracellular electron transport in *Geobacter sulfurreducens* mBio 4:e00105-13.

Malvankar, N. S., and D. R. Lovley. 2014. Microbial nanowires for bioenergy applications. Curr Opin. Biotechnol. 27:88-95.

Malvankar, N. S., S. E. Yalcin, M. T. Tuominen, and D. R. Lovley. 2014. Visualization of charge propagation along individual pili proteins using ambient electrostatic force microscopy. Nature Nanotechnology 9:1012-1017.

Derek R. Lovley and Nikhil S. Malvankar, 2015. Seeing is believing: novel imaging techniques help clarify microbial nanowire structure and function, Environmental Microbiology 7:2209-2215.

Malvankar, N. S., M. Vargas, K. P. Nevin, P.-L. Tremblay, K. Evans-Lutterodt, D. Nykypanchuk, E. Martz, M. T. Tuominen, and D. R. Lovley. 2015. Structural basis for metallic-like conductivity in microbial nanowires. mBio 6:e00084-15.

Adhikari, R. Y., N. S. Malvankar, M. T. Tuominen, and D. R. Lovley. 2016. Conductivity of individual *Geobacter* pili. RSC Advances 6:8354-8357.

Tan, Y., R. Y. Adhikari, N. S. Malvankar, S. Pi, J. E. Ward, T. L. Woodard, K. P. Nevin, Q. Xia, M. T. Tuominen, and D. R. Lovley. 2016. Synthetic biological protein nanowires with high conductivity. Small 12:doi 10.1002/smll.201601112.

There is a need for improved organic electrical conductors and systems and methods for making and using the same.

SUMMARY OF THE INVENTION

According to one aspect, the invention features an electrically conductive pilus that is produced in a strain of the microorganism *Geobacter sulfurreducens* in which the DNA sequence for PilA, the pilus monomer, has been modified in at least one location so that an aromatic amino acid is substituted in the PilA protein.

In one embodiment, at least the locations F51 and Y57 of the PilA monomer are both substituted with tryptophan.

In another embodiment, one or more of locations F24, Y27 and Y32 of the PilA monomer are additionally substituted with tryptophan.

In yet another embodiment, two or more of the locations F24, Y27, Y32, F51 and Y57 of the PilA monomer are substituted with tryptophan.

In still another embodiment, at least one amino acid encoding location in the DNA of the microorganism is substituted with a DNA sequence that encodes an aromatic amino acid in a position in which an aromatic amino acid is found in the PilA sequence from a different microorganism.

In a further embodiment, the different microorganism is a different *Geobacter* microorganism.

In yet a further embodiment, the different *Geobacter* microorganism is *Geobacter metallireducens*.

According to another aspect, the invention relates to a method of making an electrically conductive pilus, comprising the steps of: providing a microorganism capable of producing a pilus; modifying a DNA sequence of the microorganism by substituting at least one aromatic amino acid for an amino acid at the same location; growing a quantity of the microorganisms; and harvesting at least one electrically conductive pilus from the quantity of grown microorganisms.

In one embodiment, the microorganism is *Geobacter sulfurreducens*.

In another embodiment, at least two or more of the amino acids at the locations F24, Y27, Y32, F51 and Y57 in the PilA monomer are substituted with tryptophan.

In yet another embodiment, substituting at least one aromatic amino acid in the PilA monomer comprises substituting a sequence of locations with a different sequence from a different microorganism.

According to another aspect, the invention relates to a method of using an electrically conductive pilus, comprising the steps of: providing a microorganism capable of producing a pilus; modifying a DNA sequence of the microorganism by substituting the DNA sequence for at least one aromatic amino acid for the sequence of another amino acid at the same location; growing a quantity of the microorganisms; harvesting at least one electrically conductive pilus from the quantity of grown microorganisms; placing at least one of the harvested electrically conductive pilus between a pair of conductive terminals, and applying an electrical signal between the pair of electrical terminals to cause the at least one electrically conductive pilus to provide a current-voltage response.

In one embodiment, the microorganism is *Geobacter sulfurreducens*.

In another embodiment, at least two or more of the amino acids at the locations F24, Y27, Y32, F51 and Y57 are substituted with tryptophan.

In yet another embodiment, substituting at least one aromatic amino acid comprises substituting a sequence of locations with a different sequence from a different microorganism.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 1 is a schematic diagram showing the amino acid locations in an unmodified "wild-type" PilA protein filament produced by the microorganism *Geobacter sulfurreducens* with the locations F24, Y27, Y32, F51 and Y57 identified by arrows 101, 102, 103, 104 and 105 (SEQ ID NO: 19). Symbols for the various amino acid bases are listed in Table 3.

FIG. 2 is a schematic diagram showing the amino acid locations in a modified "W51W57" PilA protein filament from the microorganism *Geobacter sulfurreducens* with the locations F51 and Y57 substituted with tryptophan, and identified by arrows 204 and 205 according to principles the invention (SEQ ID NO: 20).

FIG. 12A is a current voltage (IV) response of an individual W51W57 pilus bridging two electrodes compared to the background response. An inset shows the pilus.

FIG. 12B is a current voltage (IV) response of a second individual W51W57 pilus bridging two electrodes compared to the background response. An inset shows the pilus.

FIG. 12C is a current voltage (IV) response of a third individual W51W57 pilus bridging two electrodes compared to the background response. An inset shows the pilus.

FIG. 12D is a graph of the height measurement of pili in FIG. 12A at the location designated in FIG. 12A with a white line.

FIG. 15A is an AFM image of *Geobacter sulfurreducens* wild-type pili prepared at pH 10.5 across electrodes. The white dotted line is drawn to guide the eyes.

FIG. 15B is a graph of the current-voltage response of *Geobacter sulfurreducens* wild-type pili from four probe measurement. Markers represent an average of three measurements while standard errors represent the error bars.

FIG. 15C is a graph of the current-voltage response of *Geobacter sulfurreducens* wild-type pili from two probe measurements. Markers represent an average of three measurements while standard errors represent the error bars.

FIG. 16 is a diagram showing the alignment of PilA amino acid sequences of *Geobacter sulfurreducens* (SEQ ID NO: 19) and *Geobacter metallireducens* (SEQ ID NO: 23). The aromatic amino acids at the same locations in *Geobacter sulfurreducens* and *Geobacter metallireducens* are marked with arrows pointing down, and the additional locations in *Geobacter metallireducens* having aromatic amino acids are marked with arrows pointing up.

FIG. 18A is an atomic force microscopy image of the MP pili bridging electrodes.

FIG. 18B is a graph of the diameter (height) of the MP pili as measured across the pili.

FIG. 18C is a graph showing the current-voltage response of the MP pili at pH7.

DETAILED DESCRIPTION

Figure 3:
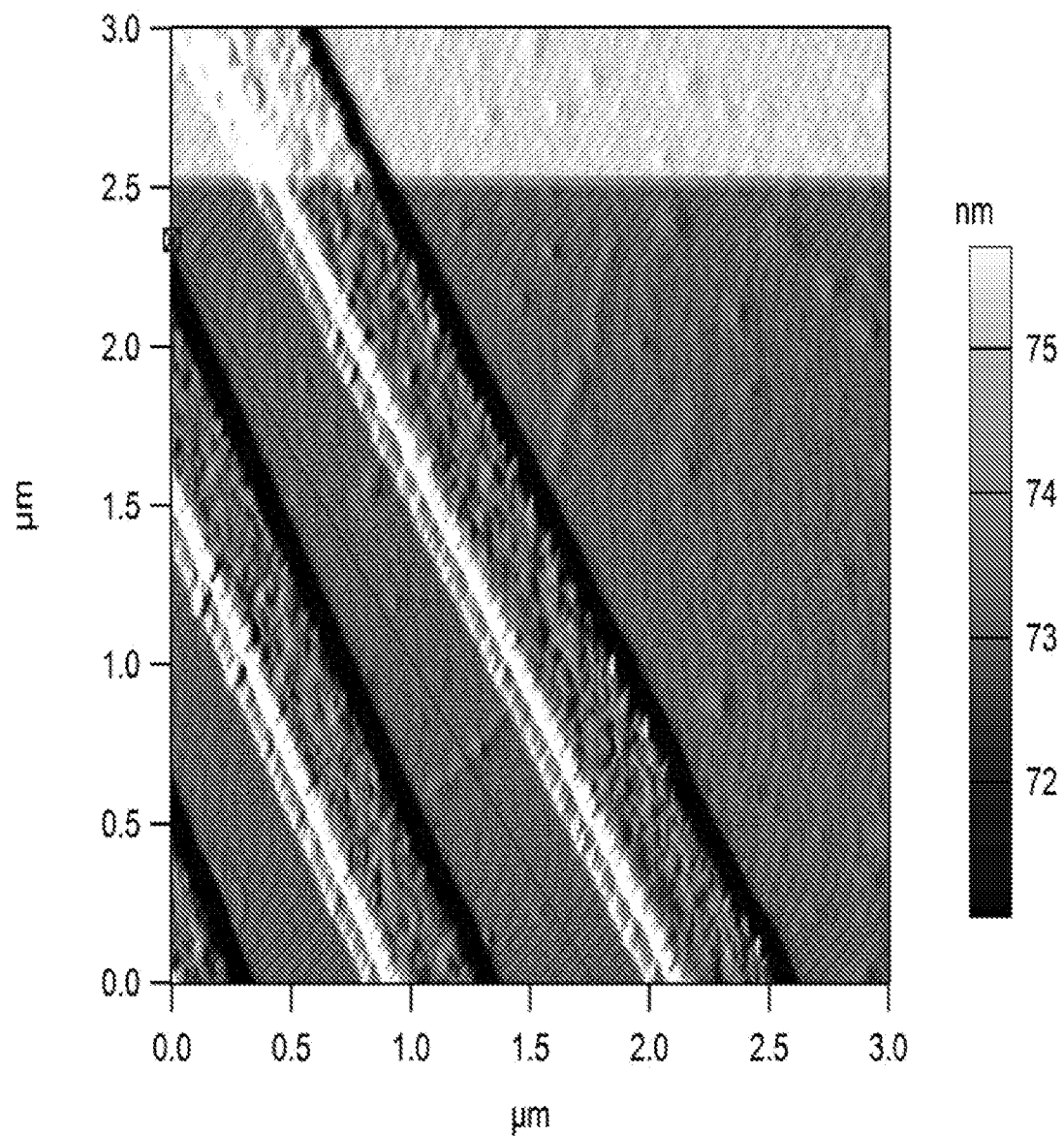
FIG. 3 is an image of "W51W57" PilA having the amino acid sequence described in FIG. 2 and prepared for conductivity measurements.

Microbial nanowires are conductive protein filaments produced by the microorganism *Geobacter sulfurreducens*. Initial properties were described in U.S. Pat. No. 7,498,155, "Microbial Nanowires Related Systems and Methods of Fabrication".

Microbial nanowires are a potential 'green' source of electronic materials. Briefly, it is now understood that microbial nanowires are conductive along their length with a metallic-like conductivity that can be attributed to pi-pi stacking of aromatic amino acids in the microbial nanowire structure. This property permits the microbial nanowires to propagate charge in a manner comparable to carbon nanotubes with comparable charge densities. The nanowires can also have transistor properties. Other desirable properties include: they are thinner (3 nm diameter) than typical nanowires made from non-biological materials; they conduct electrons over the full length (30 µm) of a single wire or they can be assembled into networks that conduct electrons over centimeter distances; they are produced with a simple 'green synthesis' with no toxic chemicals required and no toxic materials in the final product; they are very stable, much more difficult to denature than typical proteins; they are robust; they can function over a wide range of pH (2-11); and they function in water.

The possibility of a diversity of biological materials functioning as nanowires has been explored. For example, a single DNA molecule functioning as a conductive wire has the advantage of narrow diameter (2 nm) with lengths of hundreds of nanometers. However, there are large differences in the reported conductivity of DNA nanowires, and the primary application of DNA may be as a template for the patterning of metals or semi-conductive materials. Biologically produced protein fibers such as silk, actin, collagen, and amyloid fibers are also good templates for metal deposition to produce nanowires, but are otherwise poorly conductive. Synthetic peptides can form thin (nanometer) filaments, but with relatively low conductivities (<1 mS/cm). Cytochrome-rich membrane extrusions of the microorganism *Shewanella oneidensis* were electrically conductive (60 mS/cm-1 S/cm), when chemically fixed and dehydrated, but the filaments were comprised of a complex mixture of lipids and proteins, which might be difficult to standardize as a material. *G. sulfurreducens* pili are electrically conductive without chemical fixation. Charge is propagated along the pili in a manner comparable to carbon nanotubes, which has been attributed, at least in part, to the pi-pi stacking of constituent aromatic amino acids. The highest conductivity along the length of individual pili (188 mS/cm) is observed at low pH (pH 2), consistent with an observed increase in pi-pi stacking with proton doping.

Genetic substitution of an alanine for each of the three tyrosines and two of the phenylalanines in PilA, the pilus monomer, yielded pili (known as Aro-5 pili) with poor conductivity, further suggesting the importance of aromatic amino acids in electron transport.

We have reduced to practice several different genetic modifications of the amino acid sequence of PilA of *Geobacter sulfurreducens*, the protein monomer that assembles into the microbial nanowire. In some embodiments, the substitutions are accomplished as individual substitutions on defined locations of the amino acid sequence. In other embodiments, the substitutions are accomplished by replacing a plurality of amino acids with a different plurality of amino acids in which one or more amino acids differ from the corresponding sequence in the plurality that is replaced. That is, a segment comprising a plurality of amino acids is removed, and is replaced with a different segment comprising a plurality of amino acids that differs from the amino acid sequence in the segment that has been removed. Preferably, the substitutions involve the incorporation of one or more aromatic amino acid bases phenylalanine (F), tryptophan (W), tyrosine (Y), and histidine (H).

We have reduced to practice a genetic modification of substituting two tryptophans for other aromatic amino acids in PilA of *Geobacter sulfurreducens*, the protein monomer that assembles into the microbial nanowire. This modification increased the nanowire conductivity up to one million fold and cut the diameter of the pili in half. Other amino acid modifications are possible and are being evaluated to determine if conductivity can be further increased.

In particular, we have demonstrated that the substituted nanowires can be more conductive by a factor of approximately one million as compare to the unmodified nanowires.

We have demonstrated that substituting tryptophan in one or more selected location in a "wild type" or unmodified PilA can increase the conductivity of the pilus. In particular we have identified the five locations illustrated in FIG. 1 as locations where such a modification is, or is believed to be, advantageous.

FIG. 1 is a schematic diagram showing the amino acid locations in an unmodified "wild-type" PilA protein filaments produced by the microorganism *Geobacter sulfurreducens* with the locations F24, Y27, Y32, F51 and Y57 identified by arrows 101, 102, 103, 104 and 105. In the embodiment shown in FIG. 1, amino acids identified as F, Y and W are, respectively, F=Phenylalanine Y=Tyrosine W=Tryptophan. The remainder of the amino acids can be identified by using Table 3 presented herein below.

FIG. 2 is a schematic diagram showing the amino acid locations in a modified "W51W57 modification" PilA protein filament from the microorganism *Geobacter sulfurreducens* with the locations F51 and Y57 substituted with tryptophan, and identified by arrows 204 and 205, according to principles the invention.

FIG. 3 is an image of "W51W57 modification" PilA having the amino acid sequence described in FIG. 2 and prepared for conductivity measurements.

Figure 4:
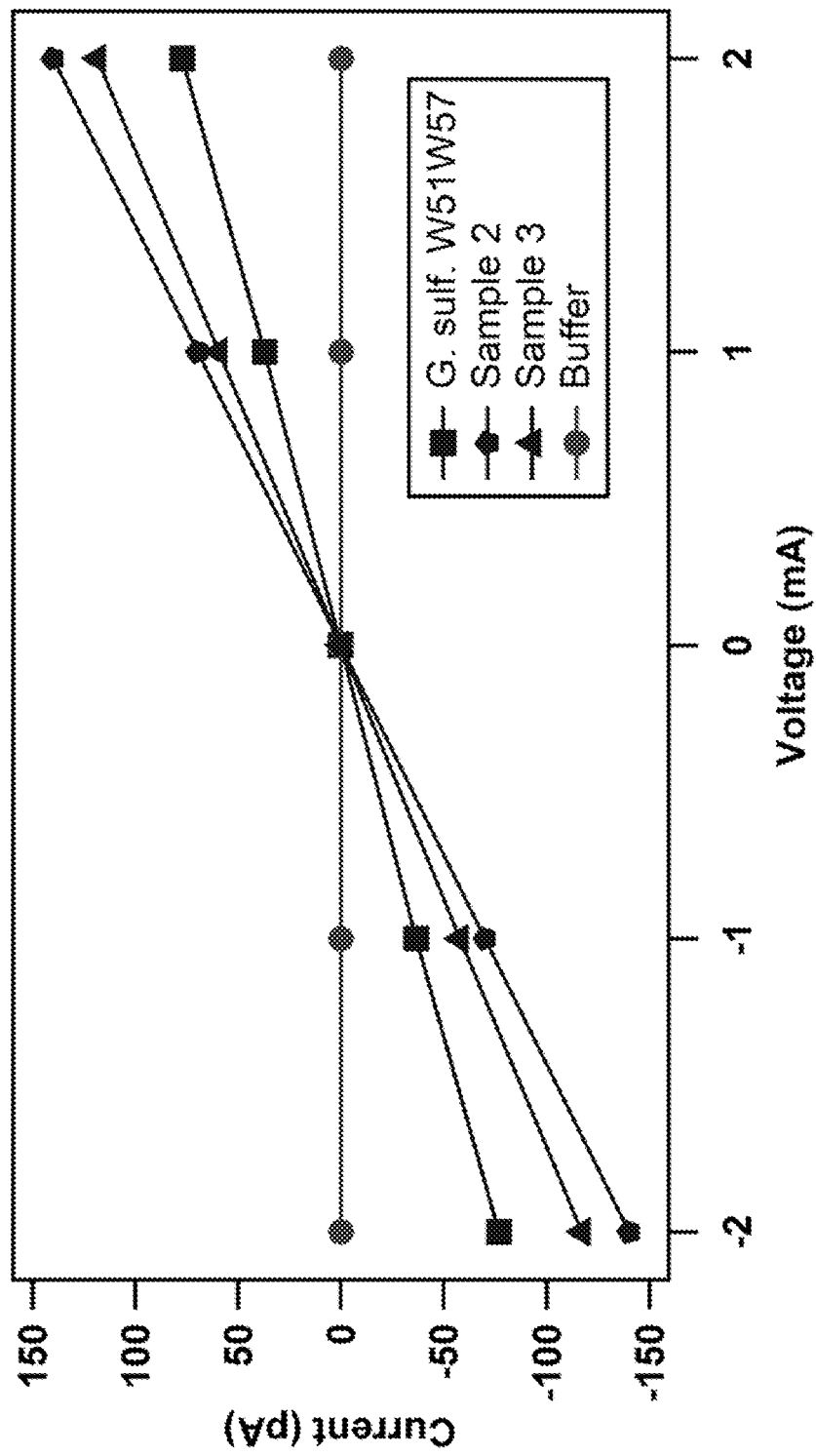
FIG. 4 is a graph showing the current voltage response of several samples of "W51W57" PilA.

FIG. 4 is a graph showing the current voltage response of several samples of "W51W57" PilA.

Our strategy to increase the conductivity of the pili of *Geobacter sulfurreducens* was based upon our understanding of the mechanisms for pili conductivity developed through biophysical, genetic, and structural studies (1-9). These studies demonstrated that the *G. sulfurreducens* pili possessed metallic-like conductivity similar to that observed in synthetic organic conducting polymers. This is remarkable because long-range electron transport via metallic-like conductivity had not previously been observed in a biological protein. These studies also demonstrated that the metallic-like conductivity could be attributed to close packing of aromatic amino acids.

The conductive *G. sulfurreducens* pili are comprised of the monomer protein PilA. Five aromatic amino acids in the PilA sequence were shown to be essential for conductivity (4). Surprisingly, none of these aromatic amino acids were a tryptophan. See FIG. 1 and FIG. 5.

Figure 5:
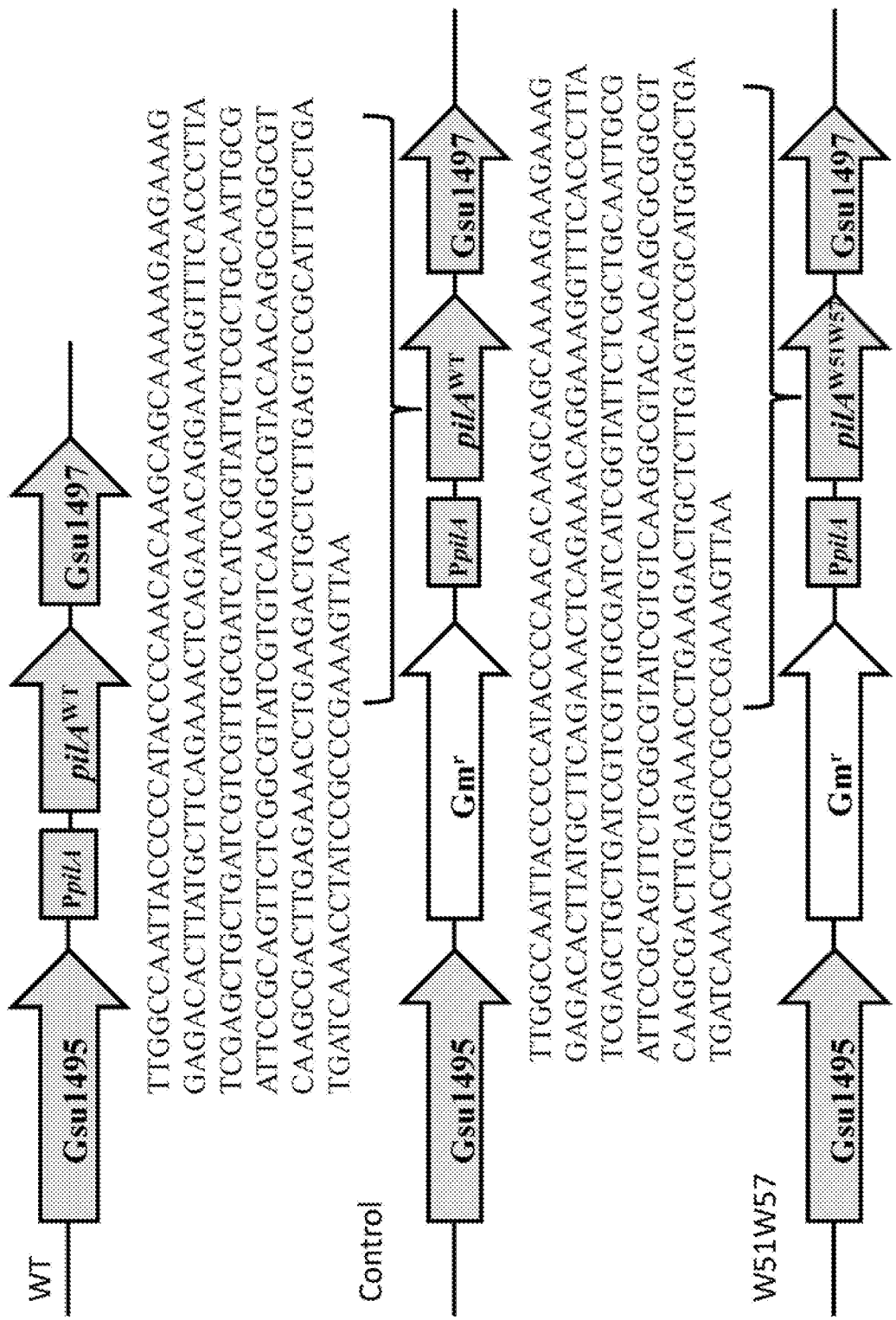
FIG. 5 is a genetic map diagram showing the gene organization around the wild-type PilA gene: the construction of a control strain containing a gentomycin resistance gene and wild-type sequence of pilA and related genes (SEQ ID NO: 21); and the W51W57 strain in which the pilA sequence was modified to encode a tryptophan at amino acid positions 51 and 57 (SEQ ID NO: 22).

FIG. 5 is a genetic map diagram showing the gene organization around the wild-type PilA gene: the construction of a control strain containing a gentomycin resistance gene and wild-type sequence of pilA and related genes; and the W51W57 strain in which the pilA sequence was modified to encode a tryptophan at amino acid positions 51 and 57.

Tryptophan is known to effectively promote short-range electron transfer in proteins (10). Therefore, we initiated studies to determine whether tryptophan might also promote long-range electron transport through a protein polymer.

As an initial strategy tryptophans were inserted at positions 51 and 57 in the PilA amino acid sequence, replacing a phenylalanine at position 51 and a tyrosine at position 57, as shown in FIG. 2, and as illustrated in the preparative description shown in FIG. 5. The overall strategy for replacing the PilA gene with a modified sequence followed previously described methods (4) (5).

The microbial strains and plasmids used to accomplish this are listed in Table 1. *Geobacter sulfurreducens* strains were routinely cultured at 30° C. under strict anaerobic conditions (80/20 $N_2$—$CO_2$) in mineral based medium containing acetate (20 mM) as the electron donor and fumarate (40 mM) as the electron acceptor (11). *Escherichia coli* Top 10 (Invitrogen, Grand Island, N.Y., USA) was cultured at 37° C. in Luria-Bertani medium and the appropriate antibiotic was added when necessary.

Strain W51W57 was constructed from *Geobacter sulfurreducens* strain PCA. The primers used for construction of strain W51W57 are listed in Table 2. Two DNA fragments were generated independently by PCR for the construction of strain W51W57 using pPLT174 as template with previously described methods (4). The wild-type allele of *G. sulfurreducens* pilA (locus tag GSU1496) was replaced on the chromosome with the mutant allele designated pilA$^{W51W57}$. As illustrated in FIG. 5, the DNA sequence of pilA$^{W51W57}$ encodes a peptide in which tryptophan (W) is substituted for phenylalanine (F) at amino acid position 51 and tryptophan (W) is substituted for tyrosine (Y) at amino acid position 57. A control strain was constructed by introducing the wild-type pilA sequence by the same methods. The structure of both the control and the mutant allele is shown in FIG. 5. The primers for PCR amplification of the wild-type pilA and the modified pilA$^{W51W5}$ are shown in Table 2.

The substitution of tryptophan into positions 51 and 57 was introduced with a 2 step PCR procedure. Briefly, the primer pair GspilAf/Trp-51-57-R was used for the PCR amplification of fragment 1 (431 bp), which included PpilA (promoter for the pilA gene) and a partial sequence (5' region) of the pilA (locus tag GSU1496) with pPLT174 as the template (4). Primer pairs Trp-51-57-F/GspilACr were used for PCR amplification of fragment 2 (602 bp) including the remainder (3' region) of pilA and the GSU1497 gene located downstream of pilA with pPLT174 as the template. Fragment 1 and fragment 2 were connected with another PCR amplification with primer pair GspilAf/GspilACr, generating DNA fragment 3, which included the PpilA, pilAW51W57 and GSU1497 coding sequences. Fragment 3 was digested by restriction enzymes XhoI and ApaI (New England Biolabs, Ipswich, Mass., USA) and then was ligated with pPLT173 (4), which was also digested by XhoI and ApaI. The ligated plasmid termed pPLT173-W51W57 was verified for sequence accuracy for the pilA$^{W51W57}$ gene by Sanger sequencing. The plasmid pPLT173-W51W57 was linearized with NcoI (New England Biolabs, Ipswich, Mass., USA). Then, the linearized plasmid was electroporated into *G. sulfurreducens* PCA as previously described (11). Transformants were selected on acetate-fumarate agar plates (11) containing gentamicin (20 μg/ml). Proper replacement of the wild-type pilA gene with pilA$^{W51W57}$ was verified with PCR amplification and DNA sequencing. The control strain containing the wild-type pilA sequence was generated with similar methods as previously described (4).

Several growth strategies can be employed for inducing the expression of *Geobacter sulfurreducens* pili (12) (13) (14) (4). For convenience, cells were grown as a biofilm on a graphite electrode serving as an electron acceptor as previously described (15). Briefly, cells were grown in a two-chambered H-cell with graphite electrodes (65 cm$^2$ solid graphite blocks, 1 in. by 0.5 in. by 3 in., grade G10, (Graphite Engineering and Sales, Greenville, Mich.) serving as the anode and the cathode. The cells grew on the anode, which was poised with a potentiostat (+300 mV versus Ag/AgCl). The cell culture in the anode chamber was initiated in medium with acetate (10 mM) as the electron donor and fumarate (40 mM) as the electron acceptor. When the culture reached an A600 density of 0.2, the anode chamber was swapped to medium with only 10 mM acetate and no fumarate. Once the current reached approximately 1 mA the system was switched to a continuous flow-through mode, in which medium was flowed through the anode chamber at a dilution rate of 0.15/hr. When the current reached 10-12 mA the biofilm was scraped from the surface of the anode into isotonic wash buffer (20.02 mM morpholinepropanesulfonic acid, 4.35 mM $NaH_2PO_4.H_2O$, 1.34 mM KCl, 85.56 mM NaCl, 1.22 mM $MgSO_4.7H_2O$, and 0.07 mM $CaCl_2.2H_2O$), then collected by centrifugation and re-suspended in 150 mM ethanolamine (pH 10.5).

To examine pili production an aliquot of cells were directly placed on copper grids coated with carbon and absorbed for 4 min. Grids with cells were negatively stained with 0.2% uranyl acetate, then examined using a JEOL 2000fxTEM operating under standard conditions at an 200 kV accelerating voltage.

Figure 6:
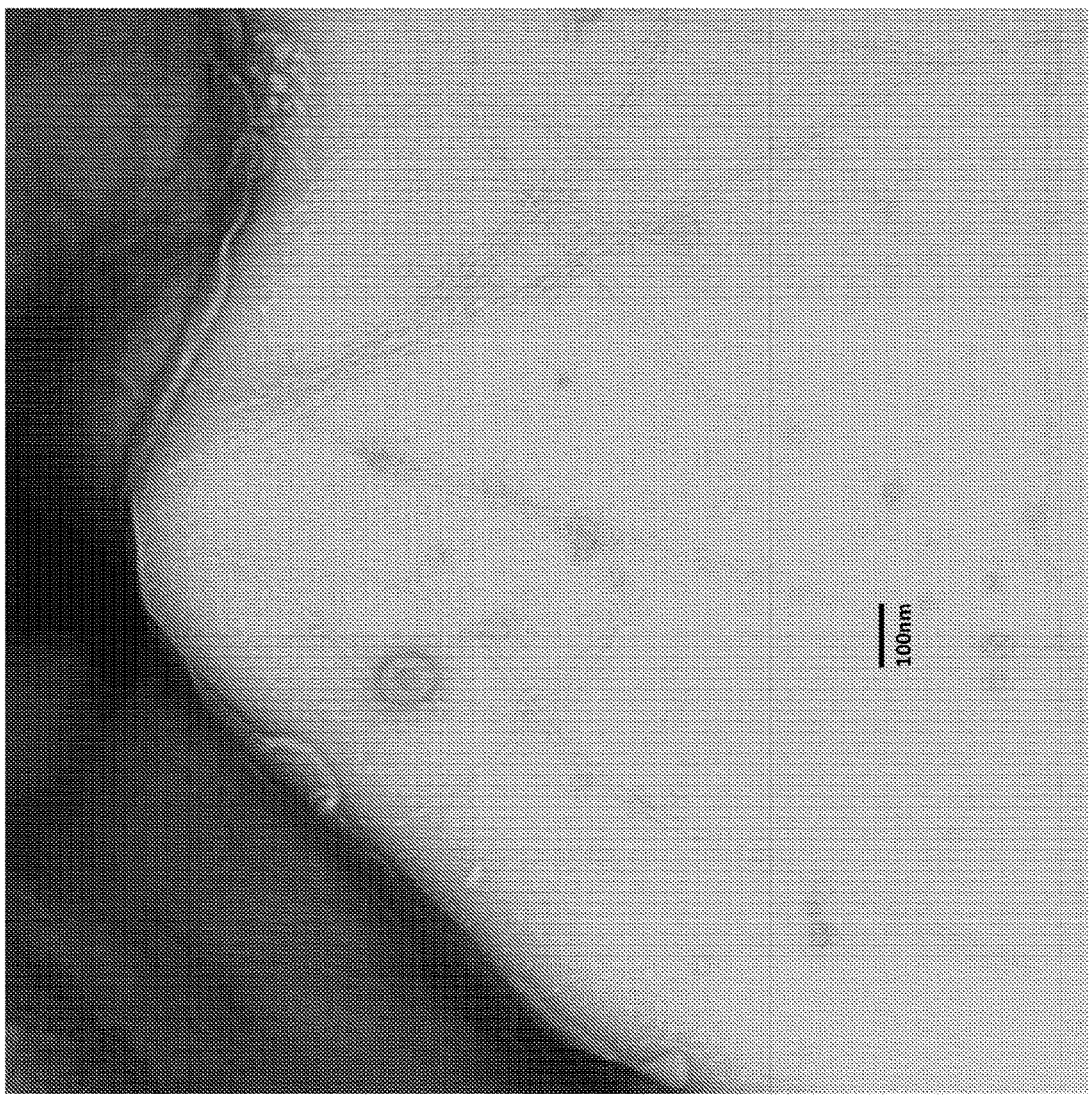
FIG. 6 is a transmission electron micrograph image of *Geobacter sulfurreducens* expressing W51W57 pili.

Transmission electron microscopy confirmed that the *Geobacter sulfurreducens* cells with the W51W57 PilA gene were expressing abundant pili similar to those typically observed on wild-type cells, as illustrated in FIG. 6, which shows *Geobacter sulfurreducens* expressing W51W57 pili.

Figure 7:
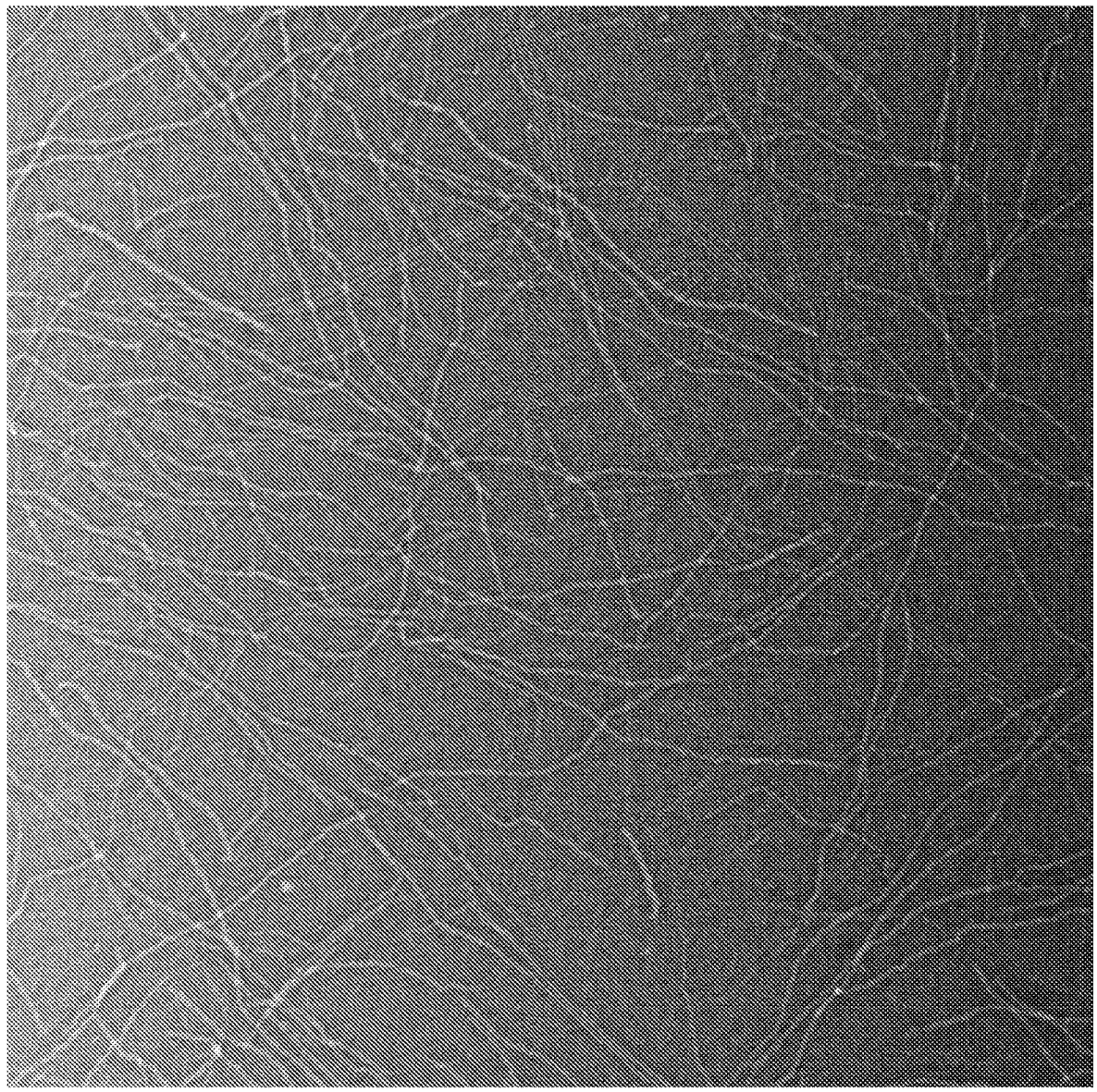
FIG. 7 is a transmission electron micrograph of a suspension of purified W51W57 pili.

Pili were mechanically sheared from the cell surface with a Waring commercial blender at low speed (~5000 rpm) for 1 min. Cell debris was removed by centrifugation at 13,000×g for 30 min at 4° C. Pili were precipitated from the supernatant with the addition of 10% ammonium sulfate for 60 min at room temperature. Pili were collected by centrifugation at 13,000×g for 60 min at 4° C., then re-suspended in 150 mM ethanolamine buffer, pH 10.5. Any additional cellular debris was removed with centrifugation at 23,000×g for 60 min at 4° C. Then the pili in the supernatant were precipitated with the addition of 10% ammonium sulfate and a 60 min room temperature incubation. Pili were then collected with centrifugation at 13,000×g for 60 min at 4° C. and then re-suspend in 150 mM ethanolamine pH 10.5. This procedure yielded highly purified pili preparations as demonstrated by transmission electron microscopy carried out as described for cells above and illustrated in FIG. 7.

A nanoelectrode array with a series of electrodes of 50 nm width separated by spacing of 50 nm was constructed in order to accurately measure the conductivity of individual pili. Copolymer methyl methacrylate (MMA-E10; Micro-Chem, Inc.) was spin-coated onto the silicon dioxide surface at 4000 rpm and baked at 180° C. for 5 minutes. This was followed by spin-coating a higher molecular weight polymethyl methacrylate (PMMA-A2) at the same speed followed by baking. Electrode patterns were written with Nanoimprint lithography and developed with a 1:3 solution of isopropanol and methyl isobutyl ketone. E-beam evaporation was used to deposit 10 nm chromium at the bottom of the electrode pattern and 20 nm gold on the top. The dimensions of the electrodes were verified with a Dektak profilometer and atomic force microscopy. The electrodes were connected to 100 µm×100 µm pads for electrical contacts.

Figure 8:
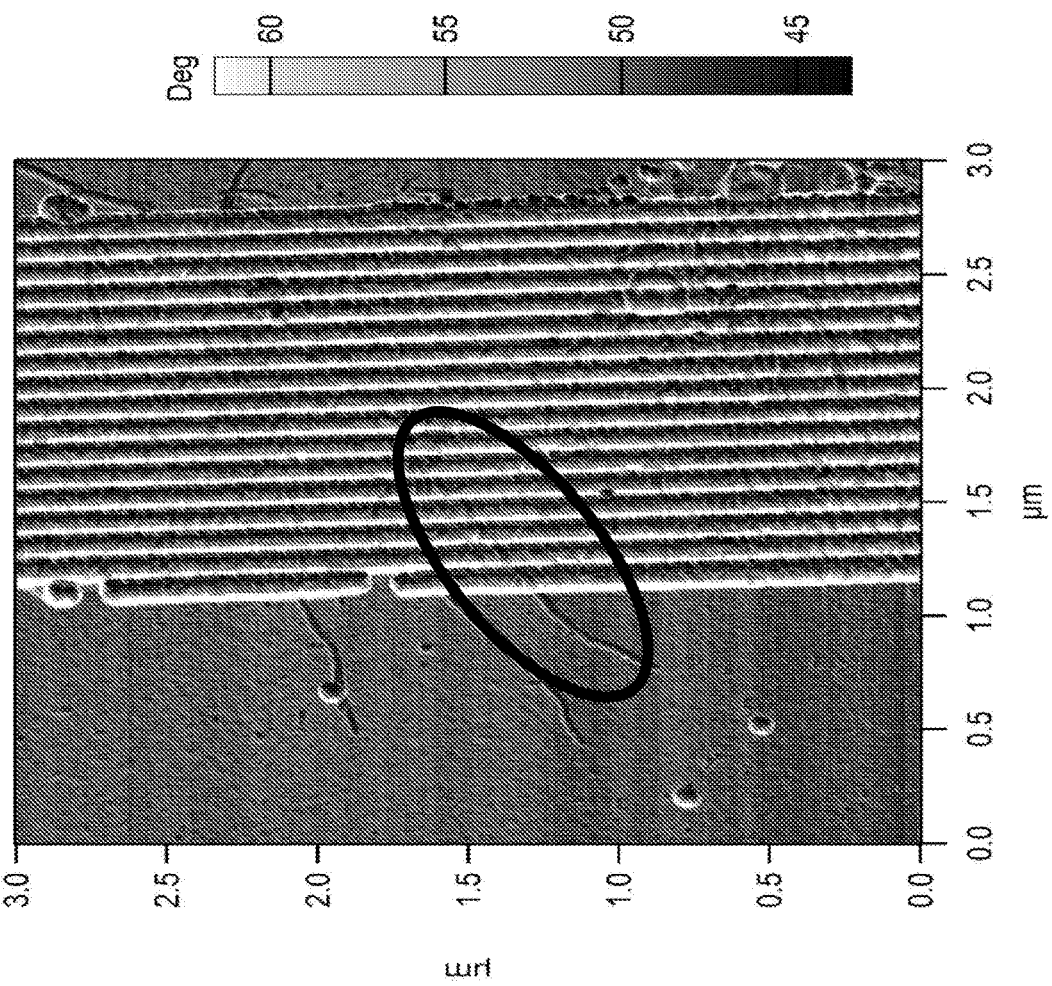
FIG. 8 is an atomic force microscope image of pili bridging a gap in an array of electrodes.

Pili in buffer were drop cast onto the electrode arrays. Pili were located with atomic force microscopy. Occasionally, a single pilus bridging two electrodes was located, as illustrated in FIG. 8, which shows an atomic force microscope image of pili bridging a gap in an electrode array. Cytochromes, which can readily be detected on pili with AFM (3), were not present on any of the filaments examined. Height measurements confirmed that each filament was a pilus, and not a flagella, which have a diameter of 12 nm.

The pads corresponding to electrodes with bridging pili were wire bonded with aluminum wire and connected to a printed circuit board. The chip containing the electrodes was placed in a double-shielded box. The outer metallic box, which served as a Faraday cage to protect the signal from external electrostatic interference, was connected to the outer grounded shield with a triaxial cable. The inner metallic box was connected to an inner low impedance guard to prevent leakage current through the circuit due to device circuitry and cabling. The central connecter terminals were connected to a circuit box placed inside the guarding box using wire soldering and gold-plated pins.

Measurements were performed with a Keithley 4200 Semiconductor Characterization System (SCS). Two Source Measure Units (SMUs) of the SCS were equipped with preamplifiers 4100-PA providing the system with capability to measure current signals with resolution of up to 100 aA (attoAmps). These SMUs were connected to the two terminals of the double-shielded box with low noise triaxial cable. Current values were recorded by grounding one of the terminals while the other terminal was set to potentials ranging from −2 V to 2 V. The current value for each applied potential was extracted by averaging the steady state measured current over time.

Figure 9:
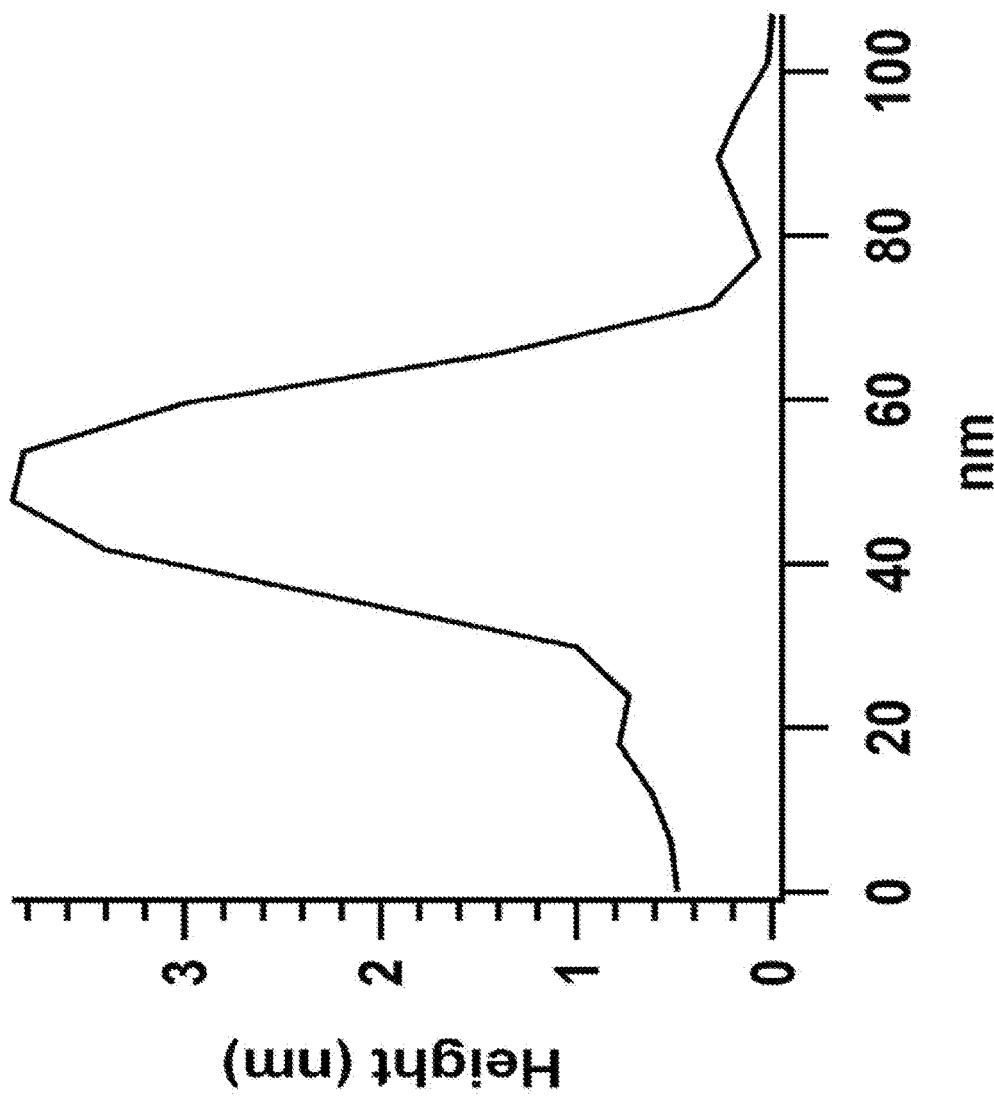
FIG. 9 is a graph that illustrates the atomic force microscopy measurement of wild-type pilus height.
Figure 10:
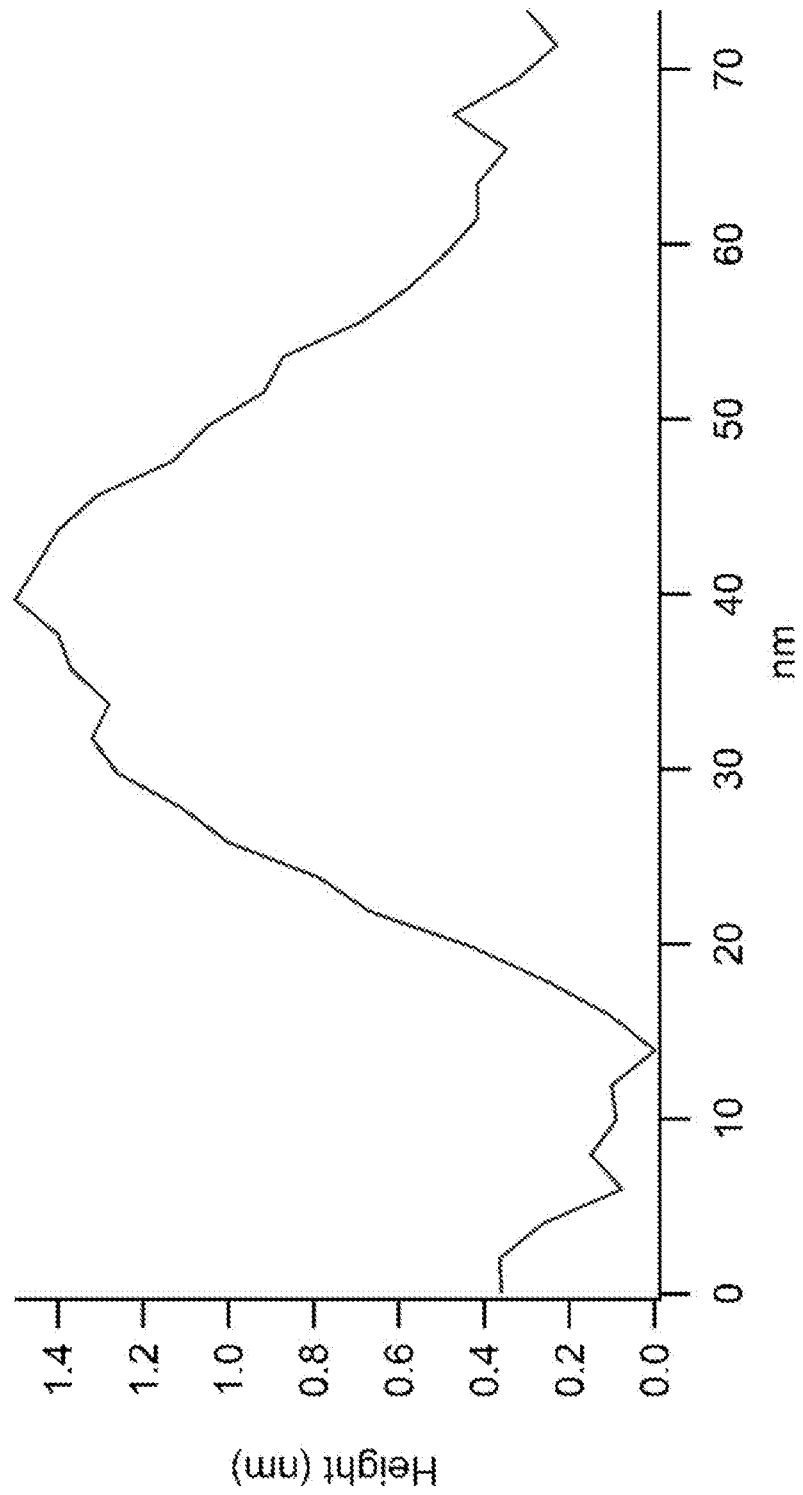
FIG. 10 is a graph that illustrates the atomic force microscopy measurement of W51W57 pilus height.

Atomic force microscopy confirmed that the height of the wild-type pili was 3 nm as expected, as shown in FIG. 9. FIG. 10 shows the height of the W51W57 pili. Surprisingly, the W51W57 pili only had a height of 1.5 nm as shown in FIG. 10.

Figure 11:
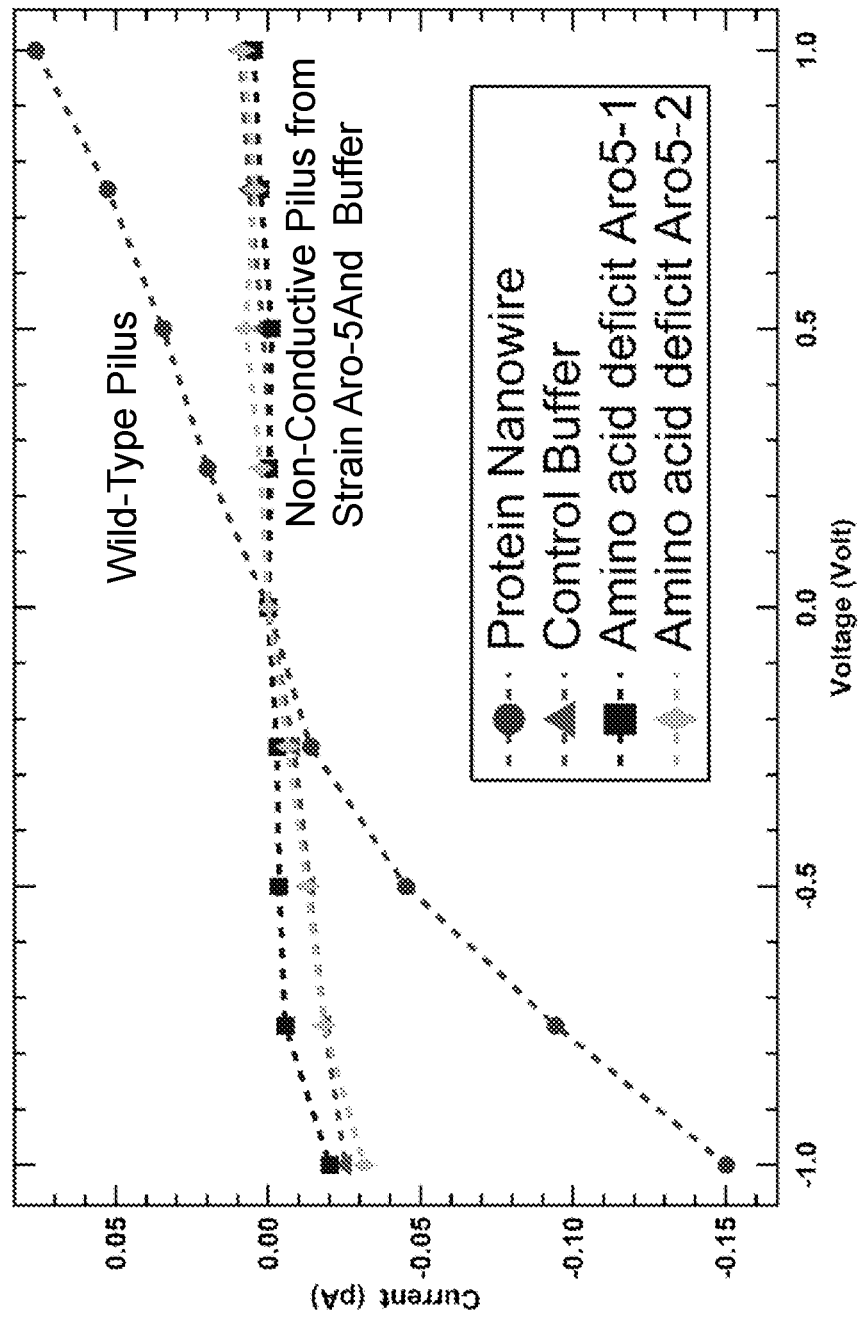
FIG. 11 is a graph showing the current voltage response of wild-type pilus, non-conductive Aro-5 pili, and buffer.

Both the wild-type pili and the W51W57 pili exhibited linear ohmic behavior. However, the W51W57 pili exhibited much higher conductance than the wild-type pili. Compare FIG. 4 with FIG. 11.

Conductivities were calculated from the relation:

$$\sigma = G \cdot \left(\frac{l}{\pi \cdot r^2}\right)$$

where, G is the conductance value acquired from the IV curve, l is the electrode gap (50 nm) and r is the radius of the pilus. The calculated conductivity of the wild-type pili was $5\times10^{-5}\pm3\times10^{-5}$ S/cm (mean±standard error of three pili), whereas the conductivity of W51W57 pili was 61±0.6 S/cm, six orders of magnitude higher than the wild-type pili.

REFERENCES

1. Malvankar N, Vargas M, Nevin K P, Franks A E, Leang C, Kim B-C, Inoue K, Mester T, Covalla S F, Johnson J P, Rotello V M, Tuominen M T, Lovley D R. 2011. Tunable metallic-like conductivity in nanostructured biofilms comprised of microbial nanowires. Nature Nanotechnology 6:573-579.
2. Malvankar N S, Lovley D R. 2012. Microbial nanowires: a new paradigm for biological electron transfer and bioelectronics. ChemSusChem 5:1039-1046.
3. Malvankar N S, Tuominen M T, Lovley D R. 2012. Lack of involvement of c-type cytochromes in long-range electron transport in microbial biofilms and nanowires. Energy. Environ. Sci. 5:8651-8659.
4. Vargas M, Malvankar N S, Tremblay P-L, Leang C, Smith J A, Patel P, Synoeyenbos-West O, Nevin K P, Lovley D R. 2013. Aromatic amino acids required for pili conductivity and long-range extracellular electron transport in *Geobacter sulfurreducens* mBio 4:e00105-00113.
5. Liu X, Tremblay P-L, Malvankar N S, Nevin K P, Lovley D R, Vargas M. 2014. A *Geobacter sulfurreducens* strain expressing *Pseudomonas aeruginosa* type I V pili localizes OmcS on pili but Is deficient in Fe(III) oxide reduction and current production. Applied and environmental microbiology 80:1219-1224.
6. Malvankar N S, Lovley D R. 2014. Microbial nanowires for bioenergy applications. Curr Opin. Biotechnol. 27:88-95.
  Malvankar N S, Yalcin S E, Tuominen M T, Lovley D R. 2014. Visualization of charge propagation along individual pili proteins using ambient electrostatic force microscopy. Nature Nanotechnology 9:1012-1017.
8. Malvankar N S, Vargas M, Nevin K P, Tremblay P-L, Evans-Lutterodt K, Nykypanchuk D, Martz E, Tuominen M T, Lovley D R. 2015. Structural basis for metallic-like conductivity in microbial nanowires. mBio 6:e00084-00015.
9. Lovley D R, Malvankar N S. 2015. Seeing is believing: novel imaging techniques help clarify microbial nanowire structure and function. Environmental microbiology (advance online publication):doi:10.1111/1462-2920.12708.
10. Shih C, Museth A K, Abrahamsson M, Blanco-Rodriguez A M, Di Bilio A J, Sudhamsu J, Crane B R, Ronayne K L, Towrie M, Vlček J, A., Richards J H, Winkler J R, Gray H B. 2008. Tryptophan-accelerated electron flow through proteins. Science 320:1760-1762.
11. Coppi M V, Leang C, Sandler S J, Lovley D R. 2001. Development of a genetic system for *Geobacter sulfurreducens*. Appl. Environ. Microbiol. 67:3180-3187.
12. Childers S E, Ciufo S, Lovley D R. 2002. *Geobacter metallireducens* accesses insoluble Fe(III) oxide by chemotaxis. Nature 416:767-769.
13. Reguera G, McCarthy K D, Mehta T, Nicoll J S, Tuominen M T, Lovley D R. 2005. Extracellular electron transfer via microbial nanowires. Nature 435:1098-1101
14. Nevin K P, Kim B-C, Glaven R H, Johnson J P, Woodard T L, Methé B A, DiDonato Jr R J, Covalla S F, Franks A E, Liu A, Lovley D R. 2009. Anode biofilm transcriptomics reveals outer surface components essential for high currency power production in *Geobacter sulfurreducens* fuel cells. PLoS ONE 4:e5628.

15. Nevin K P, Richter H, Covalla S F, Johnson J P, Woodard T L, Jia H, Zhang M, Lovley D R. 2008. Power output and columbic efficiencies from biofilms of *Geobacter sulfurreducens* comparable to mixed community microbial fuel cells. Environ. Microbiol. 10:2505-2514.

TABLE 1

| Strain or plasmid | Relevant characteristic(s) | Source or reference |
|---|---|---|
| Strains | | |
| *E. coli* | | |
| Top10 | recA1 endA1 gyrA96 thi-1 hsdR17 ($r_K^-$ $m_K^+$) supE44 relA1 ΔlacU169 | Invitrogen, Carlsbad, |
| *G. sulfurreducens* | | |
| PCA | Wild type | Lab stock |
| W51W57 | PCA Gm$^r$ pilA$^{F51W, Y57W}$ | This work |
| Plasmids | | |
| pCR2.1gm$^r$loxP | PCR cloning vector carrying gm$^r$loxP; Ap$^r$, Gm$^r$, Km$^r$ | Vargas[1] |
| pPLT173 | pCR2.1gm$^r$loxP carrying the 3' part of GSU1495 upstream of gm$^r$loxP; Ap$^r$, Gm$^r$, Km$^r$ | Vargas[1] |
| pPLT174 | pPLT173 carrying PpilA; the pilA allele; GSU1497 coding sequence; Ap$^r$, Gm$^r$, Km$^r$ | Vargas[1] |
| pPLT173-W51W57 | pPLT174 carrying the pilA$^{F51W, Y57W}$ allele; Ap$^r$, Gm$^r$, Km$^r$ | This work |
| Strains | | |
| *G. sulfurreducens* | | |
| Strain MP | PCA Gm$^r$ *G. metallireducens* pilA | This work |
| Plasmids | | |
| pACYC184 | Low-copy cloning vector carrying Tet$^r$, Cm$^r$ | Lab stock |
| pYT-1 | PACYC184 carrying the 3' part of GSU1495 upstream of gm$^r$loxP, Gm$^r$, Cm$^r$ | This work |
| pYT-1-MP | pYT-1 carrying the PpilA, *G. metallireducens* pilA allele and GSU1497 coding sequence;; Gm$^r$, Cm$^r$ | This work |

Ap$^r$, Ampicillin resistance;
Gm$^r$, Gentamicin resistance;
Km$^r$, Kanamycin;
Tet$^r$, Tetracycline;
Cm$^r$, Chlorophenol resistance.

TABLE 2

| (SEQ ID NOS 1-7, respectively, in order of appearance) | | | |
|---|---|---|---|
| Purpose | Primer name | Sequence (5' to 3') | Description |
| Recombinant pila gene construction | GspilAf | AAAAAA*CTCGAG*AGAGGAGCCAGTGACGAAAATC | Amplifies fragment1 |
| | Trp-51-57-R | CTTTCGGGCGGCCAGGTTTGATCATCAGCCCATGCCTGACTCAACTAG | |
| | Trp-51-57-F | CTCTTGAGTCCGCATGGGCTGATGATCAAACCTGGCCGCCCGAAAG | Amplifies fragment2 |
| | GspilACr | AAAAAA*GGGCCC*ACGAGACTGACCCAATCCAACAAG | |
| Transformant verification | Gs Pro | AGGAGCCAGTGACGAAAATC | |
| | Gen-screening-F | TCTTCCCGTATGCCCAACTT | |
| | GS-screening-R | ATTCCGTATTGACTCGGCTGAA | |

| (SEQ ID NOS 1 and 8-18, respectively, in order of appearance) | | | |
|---|---|---|---|
| Purpose | Primer name | Sequence (5' to 3') | Description |
| Recombinant pila gene construction for PCA GM | GspilAf | AAAAAA*CTCGAG*AGAGGAGCCAGTGACGAAAATC | Amplifies 219 bp upstream of GSU1496 for recombinant PCR |
| | GsmpilAr | GTTCCTAAGTTTCTGTAGCATAAGTGTCTCCTTTCTTCTTTT | |
| | GmpilAf | AAAAGAAGAAAGGAGACACTTATGCTACAGAAACTTAGGAAC | Amplifies both Gmet_1399 and Gmet_1400 for recombinant PCR |
| | GmpilAr | CTCCAGTATGTATTTAATCAATTAAAGTGCATTTTTCCAGTT | |

TABLE 2-continued

| | | | |
|---|---|---|---|
| | GmpilACf | AACTGGAAAAATGCACTTTAATTGATTA AATACATACTGGAG | Amplifies 500 bp downstream of |
| | GspilACr | AAACAG*GGGCCC*ACGAGACTGACCCAA TCCAACAAG | GSU1496 recombinant PCR |
| | upstream-Gen-F | AAAAAA <u>TCATGA</u> ACCGAGCTCGGATCCAGGTG | Amplifies 3' part of GSU1495 and gentamycin |
| | upstream-Gen-R | AAAAAA <u>GTCGAC</u> ATAGGGCGAATTGGGCCCTC | gene from pPLT173 |
| Transformant verification | GmpilA2f GmpilA2r GspilA3f GspilA3r | CACTTATGCTACAGAAACTTAG AATCAATTAAAGTGCATTTTC TGGACGAAATCGGAGAAGTGC CAGATGTAAGAGCCGGCAAATAC | Amplifies both Gmet1399 and Gmet1400 Amplifies 68 bp upstream and 177 bp downstream of the construct |

Vargas, M., Malvankar, N. S., Tremblay, P. L., Leang, C., Smith, J. A., Patel, P., et al. (2013). Aromatic amino acids required for pili conductivity and long-range extracellular electron transport in *Geobacter sulfurreducens*. mBio 4:e00105-13. doi:10.1128/mBio.00105-13

TABLE 3

Amino Acid Symbols

| One letter | Three letter | Amino Acid |
|---|---|---|
| A | Ala | Alanine |
| R | Arg | Arginine |
| N | Asn | Asparagine |
| D | Asp | Aspartic acid |
| B | Asx | Asn or Asp |
| C | Cys | Cysteine |
| Q | Gln | Glutamine |
| E | Glu | Glutamic acid |
| Z | Glx | Gln or Glu |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

In subsequent additional studies the genetic manipulation to substitute a tryptophan for the carboxyl terminus phenylalanine and tyrosine of PilA again yielded pili in which the diameter was reduced by half to 1.5 nm. In side-by-side comparison with wild-type pili the W51W57 pili were on average 2000 fold more conductive than the wild-type pili.

Figures 12A, 12B:
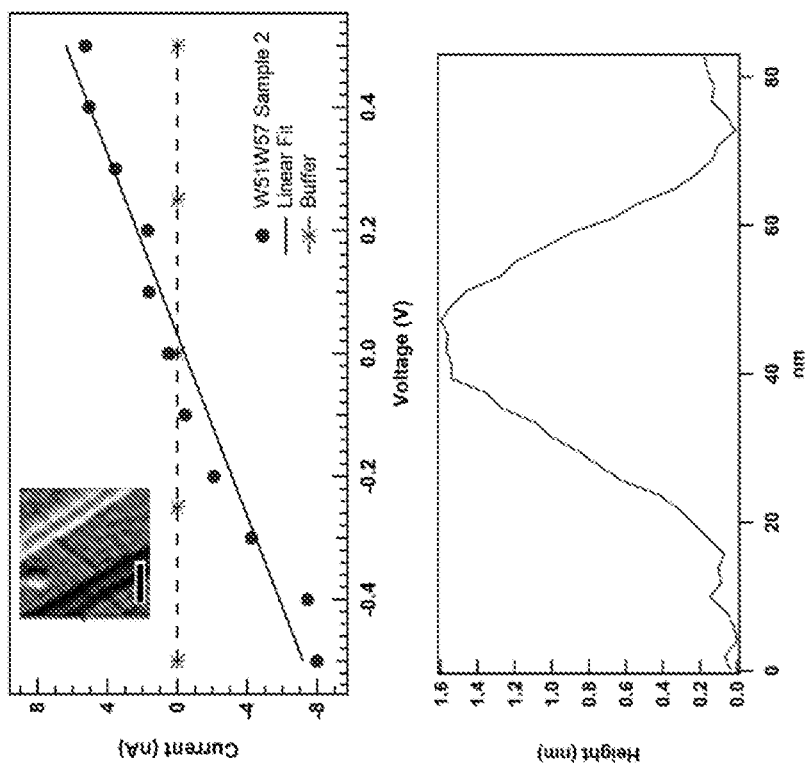
FIG. 12A through FIG. 12D summarize results from a batch of W51W57 pili produced after the batch of pili summarized in FIG. 4.
Figure 14:
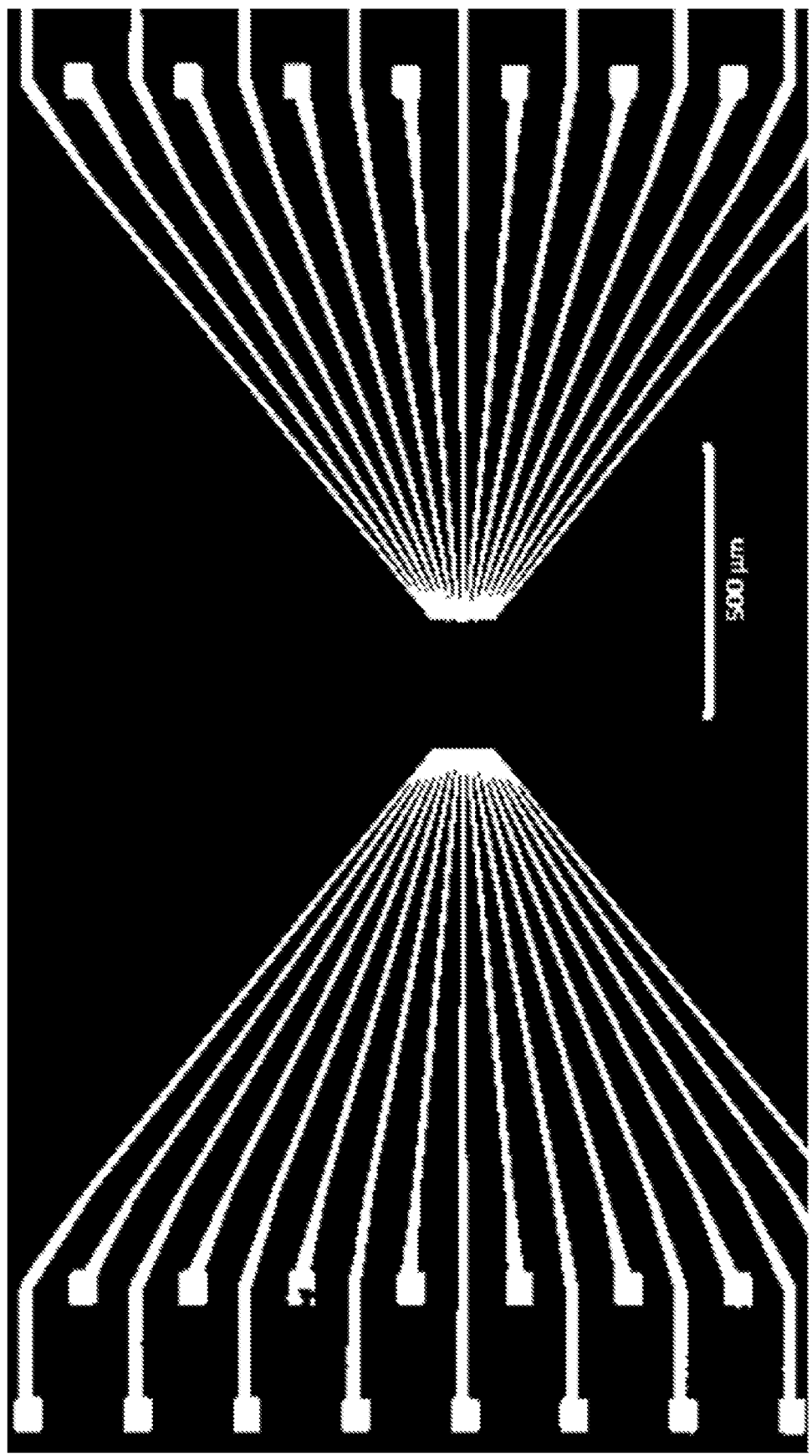
FIG. 14 is an optical image of the electrodes fabricated by nano-imprint lithography. Nanoscale electrodes (50 nm width with separation of 50 nm) fan out to microscale patterns and eventually to the contact pads.
Figure 17:
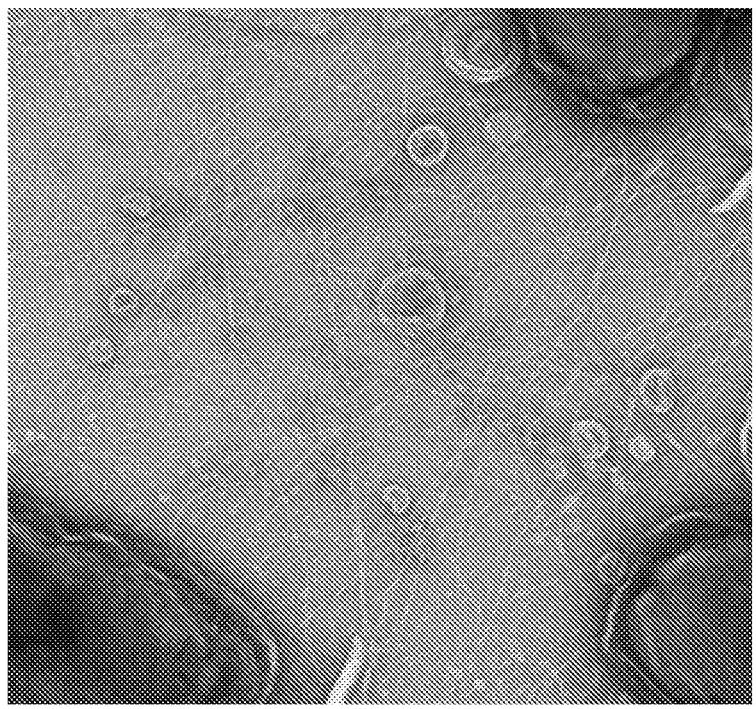
FIG. 17 is a transmission electron micrograph of *G. sulfurreducens* strain MP expressing abundant pili.

Pili harvested from the cells were dropcast on chips with multiple sets of electrodes prepared with nano-imprint lithography (FIG. 14). Single pili bridging electrodes were identified with atomic force microscopy (FIG. 12).

Figures 12C, 12D:
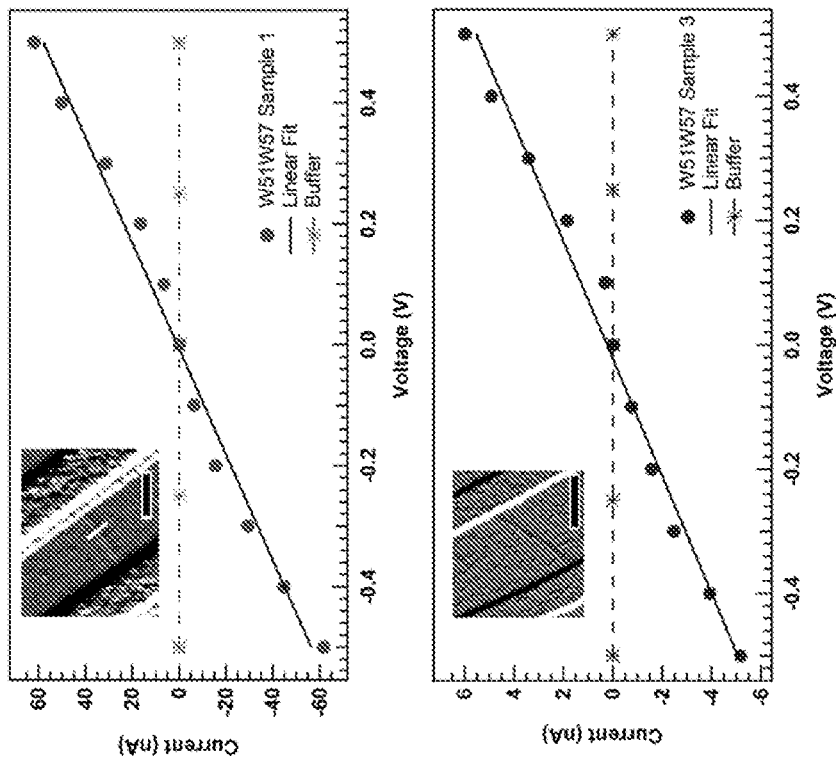

The diameter of the W51W57 pili was only 1.5 nm, half that of the native wild-type pili (FIG. 12D).

The measurement of the conductivity of such thin protein filaments with a method that does not chemically modify their structure requires care. Measurements with the low-noise nano-electrode platform yielded estimates of wild-type pili conductivity similar to previous estimates with four-probe and two-probe measurements giving similar results (FIG. 15). Two-probe methods provide good approximations of intrinsic electrical properties for nanowires with high resistances like those of the pili, especially if there is an ohmic response. Therefore, detailed analysis of the conductivity of the W51W57 pili was conducted with two-probe measurements.

Figures 13A, 13B:
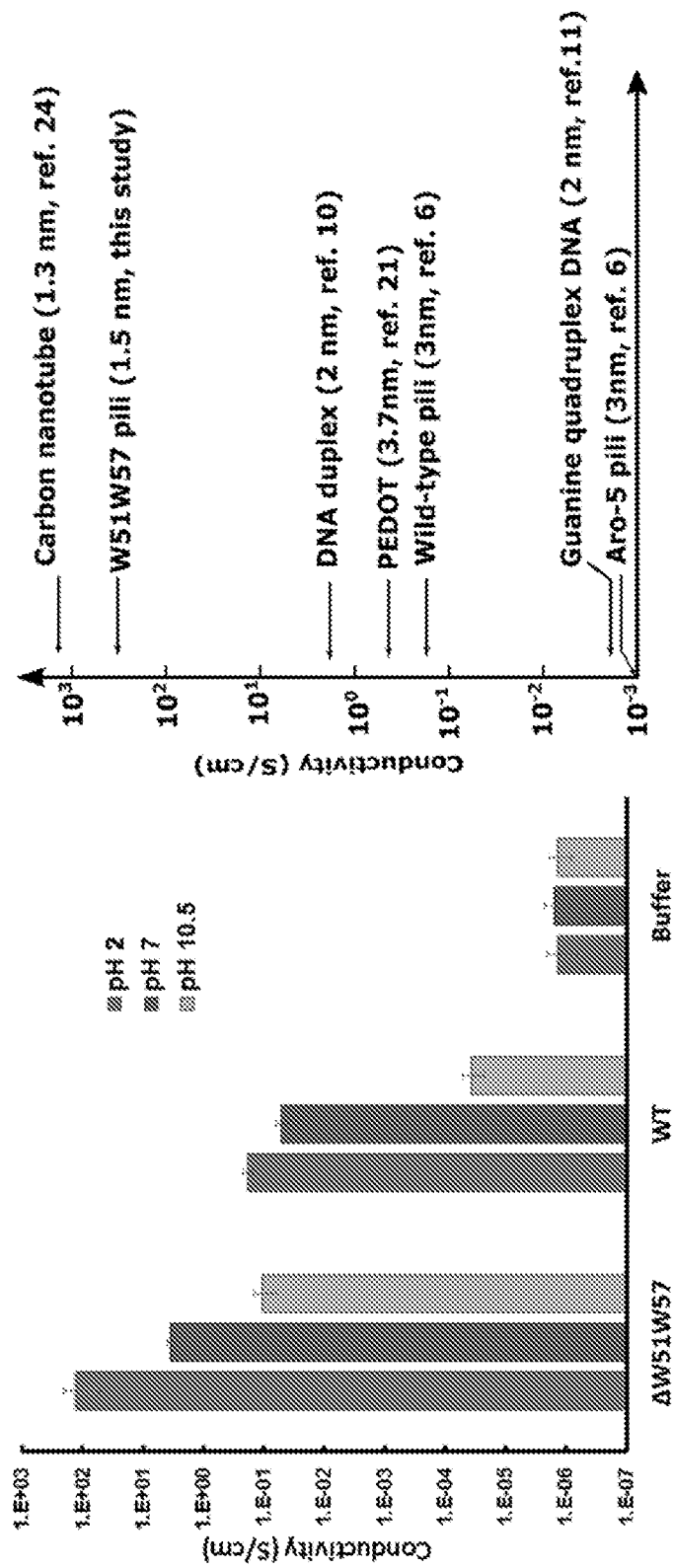
FIG. 13A is a bar graph that illustrates the effect of pH on the conductivity of strain W51W57 pili. Previously published conductivity values for wild-type are provided for comparison. The three bars are for pH 2, pH 7 and pH 10.5 from the left to the right for each type of pili.
FIG. 13B is a graph that illustrates the conductivity of strain W51W57 pili compared with the conductivities of other organic nanowires of similar diameter.

The W51W57 pili were significantly more conductive than the wild-type pili. The conductivity of the W51W57 pili increased substantially with increased proton doping (FIG. 13A). The conductivities calculated from the linear current-voltage response of three W51W57 pili prepared at pH 2 were 977±41 S/cm (FIG. 12A); 115±8 S/cm (FIG. 12B) and 90±4 S/cm (FIG. 12C). Such a broad variability in estimates of conductivity has been observed in previous studies of synthetic organic nanowires as well as other types of biological nanowires and may arise from inhomogeneity in the nanowires that dominate transport at the nanoscale. However, even the lowest conductivity estimate for the W51W57 pili represents a nearly 500-fold increase in conductivity over the wild-type pili and the mean values differ by 2000-fold (FIG. 13A).

There were also substantial differences between the conductivity of the W51W57 pili and wild-type pili prepared at higher pH (FIG. 13A). The impact of pH on conductivity of wild-type pili has attributed to increased packing of aromatic amino acids at lower pH as well as contributions of charged amino acids to electron conduction.

An important consideration for the practicality of microbial nanowires is whether they can match the conductivity of other organic conductive materials. Given the known impact of diameter on conductivity of organic nanowires, it is most appropriate to compare materials with similar diameter. When compared with two-probe measurements of other materials of similar diameter, the conductivity of the W51W57 pili prepared at pH 2 is somewhat lower than that of carbon nanotubes, but is substantially more conductive than DNA or PEDOT (poly(3,4-ethylenedioxythiophene)) nanowires (FIG. 13B).

The simultaneous reduction in diameter and increase in conductivity associated with genetic modification reported here demonstrate just some of the possibilities for improving the properties of electrically conductive pili. It is believed that the pili can be modified to enhance binding of a diversity of materials or conjugation with polymers. The ability to mass-produce such thin conductive filaments with consistent uniform diameters, morphology, and composition with simple renewable feedstocks could be an attractive option for nanowire synthesis.

Electrode Fabrication

The electrodes were made on a heavily doped silicon substrate with 1 μm thick thermal oxide with nanoimprint lithography. The substrate was cleaned with a Piranha solution ($H_2SO_4:H_2O_2=3:1$) and a diluted HF solution before patterning. After the cleaning steps, a double layer of resists (50 nm thick poly(methyl methacrylate) (PMMA) and 60 nm thick UV-curable resist) were sequentially spin-coated on the substrate. Circuit patterns including 50 nm nanoelectrodes separated by 50 nm gaps, microscale fanouts, and contact pads were transferred from a quartz mold to the UV resist with nanoimprint lithography in a homemade imprint chamber. The residual UV-resist layer and the PMMA underlayer were removed in fluorine based ($CHF3/O_2$) and oxygen based reactive ion etching, respectively. Thin films of 5 nm thick titanium and 15 nm thick gold were then deposited in an electron beam evaporator, followed by a liftoff process in acetone with ultrasonication.

Conductivity Measurements

Pili preparations in ethanolamine buffer (2 μl) were drop casted on the electrodes, washed with deionized water, air dried, treated with pH 2 buffer, and then air dried in desiccator at room temperature (22° C.) for analysis. Pili on the electrode array were located with atomic force microscopy (Asylum Research).

Alternative Embodiments

The electrically conductive pili (e-pili) of *Geobacter sulfurreducens* serve as model for a novel strategy for long-range extracellular electron transfer and a new class of bioelectronic materials. The e-pili of *Geobacter* species are of interest because of their important role in extracellular electron transport and because they represent a new form of electronic material that can be sustainably produced from inexpensive feedstocks. Previous studies on *Geobacter* e-pili have primarily focused on the pili of *Geobacter sulfurreducens*, the *Geobacter* species that has been the main focus of studies on electron transport mechanisms in *Geobacter* species.

However, the only other *Geobacter* pili studied, from *Geobacter uraniireducens*, were poorly conductive (Tan, Y., R. Y. Adhikari, N. S. Malvankar, J. E. Ward, K. P. Nevin, T. L. Woodard, J. A. Smith, O. L. Snoeyenbos-West, A. E. Franks, M. T. Tuominen, and D. R. Lovley. 2016. The low conductivity of *Geobacter uraniireducens* pili suggests a diversity of extracellular electron transfer mechanisms in the genus *Geobacter*. Frontiers in Microbiology 7:980). In order to obtain more information on the range of pili conductivities in *Geobacter* species, the pili of *Geobacter metallireducens* were investigated. Heterologously expressing the PilA gene of *G. metallireducens* in *G. sulfurreducens* yielded a *G. sulfurreducens* strain, designated strain MP, that produced abundant pili. Individual MP pili prepared at the physiologically relevant pH 7 had a conductivities of 277±18.9 S/cm, which is 5000-fold higher than the conductivity of *G. sulfurreducens* pili at pH 7, and nearly a million-fold higher than the conductivity of *G. uraniireducens* pili at the same pH. A potential explanation for the higher conductivity of the MP pili is their greater density of aromatic amino acids, which are known to be important components in electron transport along the length of the pili. The results further support the concept that the truncated PilA sequences found in many *Geobacter* species and some closely related microorganisms yield electrically conductive pili. The MP pili represent the most highly conductive pili found to date and suggest strategies for designing synthetic pili with possibly even higher conductivities.

A possible explanation for the poor conductivity of the *G. uraniireducens* pili could be that its PilA pilus monomer is much longer than the *G. sulfurreducens* PilA. The available evidence suggests that the shorter PilA of *G. sulfurreducens* permits tighter packing of the monomer, which promotes electron transfer between aromatic amino acids. Multiple lines of evidence suggest that the pili of *G. sulfurreducens* have a metallic-like conductivity, similar to that observed in synthetic conducting organic polymers, which can be attributed to overlapping pi-pi orbitals of the aromatic amino acids. Deleting one or more aromatic amino acid from PilA negatively impacts on pilus conductivity. Larger PilA monomers, such as those found in *G. uraniireducens* and *Pseudomonas aeruginosa* may prevent the tight packing required for close association of aromatic amino acids.

Materials and Methods

Bacterial Strains, Plasmids, and Culture Conditions

All bacterial strains and plasmids used are summarized in Table 1 in the supplemental material. The *G. sulfurreducens* strain was routinely cultured at 30° C. under strict anaerobic conditions (80/20 $N_2$—$CO_2$) in mineral based medium containing acetate (15 mM) as the electron donor and fumarate (40 mM) as the electron acceptor, as previously described (Coppi et al. 2001). Chemically competent *E. coli* TOP10 (Invitrogen, Grand Island, N.Y., USA) was used routinely for cloning and cultured at 37° C. in Luria-Bertani medium and the appropriate antibiotic was added when necessary.

Construction of *G. sulfurreducens* Strain MP

The strain MP was constructed from *G. sulfurreducens* PCA using the same general approach described above for producing the W51W57 pili. Primers used for construction of strain MP are listed in Table 2. The three DNA fragments were generated independently by PCR for the construction of the strain MP. Primer pair GspilAf/GsmpilAr amplified the promoter region of the pilA gene using pPLT174 as the template for the generation of fragment 1. For the generation of fragment 2, primer pair GmpilAf/GmpilAr amplified pilA-N (locus tag Gmet_1399) and pilA-C (locus tag Gmet_1400) using *G. metallireducens* GS15 genomic DNA as the template. Primer pair GmpilACf/GspilACr amplified 500 bp downstream of the pilA gene using *G. sulfurreducens* PCA genomic DNA as the template for the generation of fragment 3. Three independent fragments for strain MP were combined via recombinant PCR with primer pair GspilAf/GspilACr as previously described in Liu et al. 2014 (Liu, X., P.-L. Tremblay, N. S. Malvankar, K. P. Nevin, D. R. Lovley, and M. Vargas. 2014. A *Geobacter sulfurreducens* strain expressing *Pseudomonas aeruginosa* type IV pili localizes OmcS on pili but Is deficient in Fe(III) oxide reduction and current production. Appl Environ Microbiol 80:1219-1224.)

The plasmid pYT-1 was constructed for the construction of strain MP. The construction of pYT-1 followed the steps below. One fragment containing 3' part of GSU1495 and gentamycin gene were amplified from pPLT173 with primer pair upstream-Gen-F and upstream-Gen-R. And the fragment was digested by SalI and BspHI(NEB) and the generated fragment was ligated with pACYC184 digested by the SalI and BspHI. Based on that procedure, we constructed pYT-1. The recombinant PCR products for strain MP were digested with XhoI and Apa I and ligated with the pYT-1 digested by XhoI and Apa I. The generated pYT-1-MP was linearized with ScaI (NEB) and electroporated into PCA competent cells (Coppi et al. 2001). The transformants selection and verification follows the steps as previously described by Liu et al. 2014.

Pili Preparation

*G. sulfurreducens* strain MP was grown as biofilm on graphite electrodes which served as the electron acceptor for acetate oxidation. Cells were gently scraped from the surface using a plastic spatula and isotonic wash buffer (20.02 mM morpholinepropanesulfonic acid, 4.35 mM $NaH_2PO_4.H_2O$, 1.34 mM KCl, 85.56 mM NaCl, 1.22 mM $MgSO_4.7H_2O$, and 0.07 mM $CaCl_2.2H_2O$). The cells were collected by centrifugation and re-suspended in 150 mM ethanolamine (pH 10.5). A Warning Commercial Blender was used to mechanically shear the pili from the cell surface at low speed for 1 min, and then cells were removed with centrifugation at 13,000 g. The pili in the supernatant were precipitated with 10% ammonium sulfate overnight and collected with centrifugation at 13,000 g. In order to further purify the pili, the precipitate was re-suspended in ethanolamine buffer and debris were removed by subsequent centrifugation at 23,000 g. The pili were collected with a second 10% ammonium sulfate precipitation and subsequent centrifugation at 13,000 g. The final pili preparation was re-suspended in the ethanolamine buffer and stored at 4° C.

For the Transmission Electron Microscopy, the cells in the anode biofilm were placed on 400 mesh carbon coated copper grids, and incubated for 5 min for adsorption of the sample to the grid. The grids were negatively stained with 2% uranyl acetate. Samples were examined using a Tecnai 12 transmission electron microscope operated at 100 kV, and images were taken with a Teitz TCL camera.

Pili Conductivity Measurements

Pili preparations in ethanolamine buffer (2 µl) were drop casted on the electrodes. After waiting for a few minutes to allow pili to settle, the residual solution was withdrawn with a micropipette. Deionized water was used to remove the electrolytes. Then, the samples were gently air dried at room temperature (22° C.) for analysis. Aqueous HCl was used to adjust pH environment surrounding pili. The atomic force microscope (Asylum Research) was used to locate pili on the electrode array. The chip containing electrodes with pili was placed in a double-shielded box for low current measurements and the Keithley 4200 Semiconductor Characterization System (SCS) was used to characterize the I-V curve for the pili.

Pili Conductivity

Individual MP pili bridging the non-conductive gap between electrodes on an electrode array (FIG. 18A) had a height of 3 nm (FIG. 18B). Conductivity was determined at pH 7 for physiological relevance. The individual pili had a linear ohmic response in current over a small, physiologically relevant voltage span (FIG. 18). The conductivity of the MP pili was 277±18.9 S/cm (mean±standard deviation for three pili).

Figure 19:
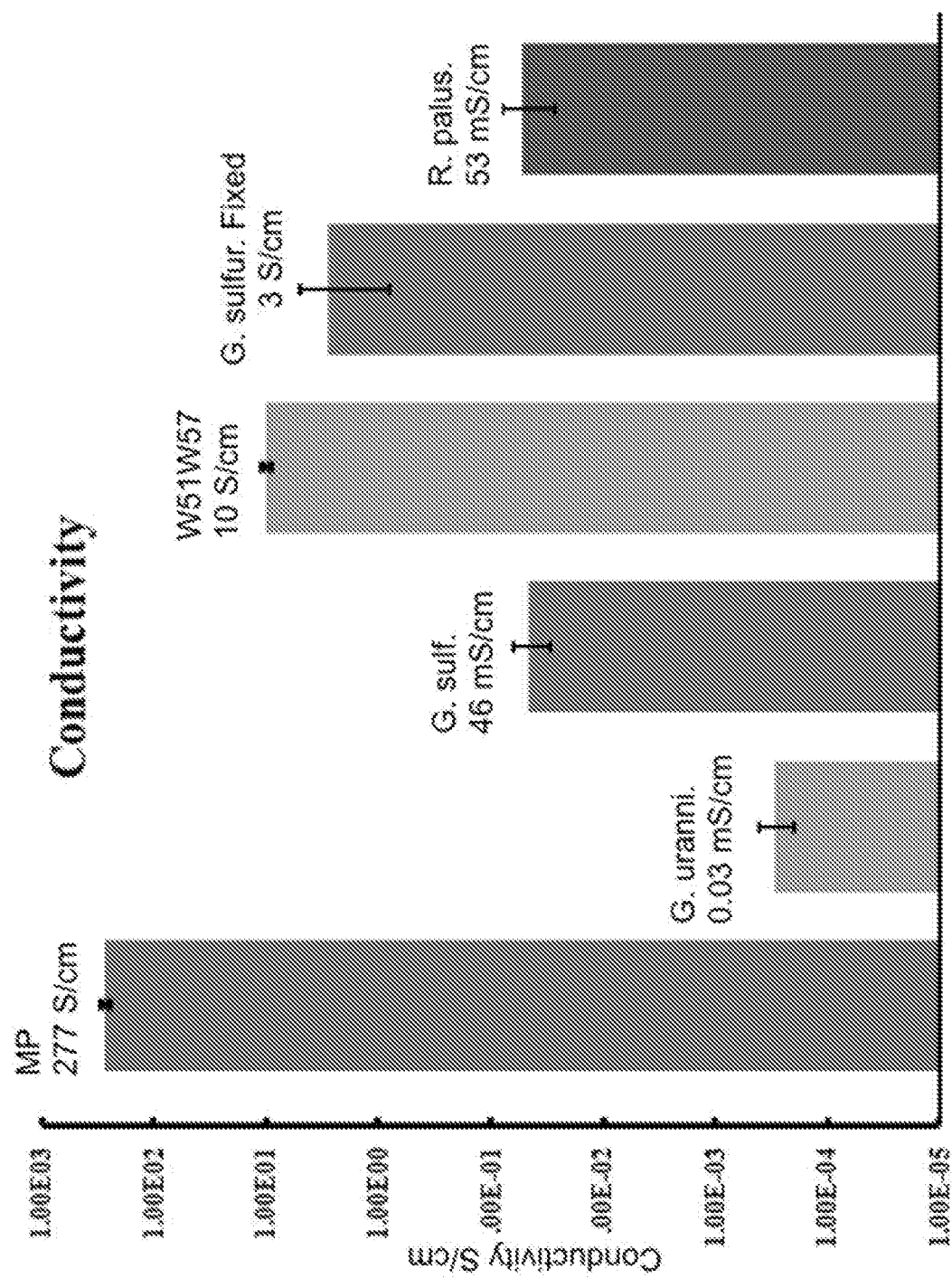
FIG. 19 is a bar graph that compares the conductivity of conductive filaments among MP pili, *Geobacter uraniireducens* pili, wild-type *Geobacter sulfurreducens* pili, W51W57 pili, chemically fixed *Geobacter sulfurreducens* pili, and *Rhodopseudomonas palustris* filaments.

The conductivity of the MP pili at pH 7 is 5000-fold higher than the conductivity of *G. sulfurreducens* pili prepared under similar, physiologically relevant conditions and nearly a million-fold higher than the conductivity of *G. uraniireducens* pili (FIG. 19). It is also higher than the synthetic W51W57 pili in which a phenylalanine and a tyrosine in the *G. sulfurreducens* PilA were replaced with tryptophan (FIG. 19). Chemical treatments of pili such as preparing them at pH 2 can dramatically increase their conductivity, but even at pH 7 the MP pili are more conductive than the *G. sulfurreducens* pili prepared at pH 2 (0.2 S/cm) and nearly as high as the conductivity of the synthetic pili W51W57 at pH 2. Estimates of conductivity along the length of *G. sulfurreducens* pili prepared in solvents and dried, were somewhat higher than the estimate for *G. sulfurreducens* obtained without such harsh chemical conditions (FIG. 19), but still orders of magnitude lower than the conductivity of the MP pili. *Rhodopseudomonas palustris* filaments of unknown composition thought to be involved in extracellular electron transfer had much lower conductivities (FIG. 19), but these filaments were also chemically fixed and dried, which may have affected their conductivity.

The results demonstrate that not only are the MP pili electrically conductive, but are much more conductive than those of *G. sulfurreducens*. The higher conductivity of the MP pili suggests it may be a superior material for the construction of electronic devices. The higher conductivity of the MP pili is associated with a greater density of aromatic amino acids in the *G. metallireducens* PilA (FIG. 16). Aromatic amino acids contribute to pili conductivity and the additional aromatic amino acids may provide more or better paths for electron transport. It is believed that pili with even higher conductivities may be obtained by further increasing the aromatic amino acid content of the PilA with genetic manipulation.

In various embodiments studied to date there has periodically been observed a nearly million-fold range in conductivity of *Geobacter* pili (FIG. 19).

Definitions

Any reference in the claims to an electronic signal or an electromagnetic signal (or their equivalents) is to be understood that in a preferred embodiment the signal is a non-transitory electronic signal or a non-transitory electromagnetic signal. If the signal per se is not claimed, the reference may in some instances be to a description of a propagating or transitory electronic signal or electromagnetic signal.

Unless otherwise explicitly recited herein, any reference to "record" or "recording" is understood to refer to a non-volatile or non-transitory record or a non-volatile or non-transitory recording.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. An electrically conductive pilus comprising a plurality of modified *Geobacter sulfurreducens* PilA monomers, wherein each modified PilA monomer comprises an amino acid sequence that differs from SEQ ID NO: 19, the amino acid sequence of the wild-type *Geobacter sulfurreducens* PilA monomer, by the substitution of at least the amino acids at positions F51 and Y57 of SEQ ID NO: 19 with tryptophan, and wherein the electrically conductive pilus has greater conductivity than a wild-type *Geobacter sulfurreducens* pilus.

2. The electrically conductive pilus of claim 1, wherein one or more amino acids at positions F24, Y27 and Y32 of SEQ ID NO: 19 are additionally substituted with tryptophan in each modified PilA monomer.

3. A method of making the electrically conductive pilus of claim 1, comprising the steps of: providing a microorganism capable of producing a pilus; modifying a DNA sequence of said microorganism to encode a modified PilA monomer that comprises an amino acid sequence that differs from SEQ ID NO: 19 by the substitution of at least the amino acids at positions F51 and Y57 of SEQ ID NO: 19 with tryptophan; growing a quantity of said microorganisms; and harvesting at least one electrically conductive pilus from said quantity of grown microorganisms.

4. The method of making an electrically conductive pilus of claim 3, wherein said microorganism is *Geobacter sulfurreducens*.

5. The method of making an electrically conductive pilus of claim 3, wherein substituting the DNA sequence encoding tryptophan in the PilA monomer comprises substituting a sequence from a different microorganism.

6. A method of using the electrically conductive pilus of claim 1, comprising the steps of: providing a microorganism capable of producing a pilus; modifying a DNA sequence of the microorganism to encode a modified PilA monomer that comprises an amino acid sequence that differs from SEQ ID NO: 19 by the substitution of at least the amino acids at positions F51 and Y57 of SEQ ID NO: 19 with tryptophan; growing a quantity of said microorganisms; harvesting at least one electrically conductive pilus from said quantity of grown microorganisms; placing at least one of the harvested electrically conductive pilus between a pair of conductive terminals, and applying an electrical signal between said pair of electrical terminals to cause said at least one electrically conductive pilus to provide a current-voltage response.

7. The method of using an electrically conductive pilus of claim 6, wherein said microorganism is *Geobacter sulfurreducens*.

8. The method of using an electrically conductive pilus of claim 6, wherein substituting the DNA sequence encoding tryptophan comprises substituting a sequence from a different microorganism.

9. The electrically conductive pilus of claim 1, wherein the pilus has a diameter of less than 3 nm.

10. The electrically conductive pilus of claim 9, wherein the pilus has a diameter of about 1.5 nm.

11. The electrically conductive pilus of claim 1, wherein the pilus is about one million-fold more conductive than a wild-type *Geobacter sulfurreducens* pilus.

* * * * *